United States Patent [19]
Masato et al.

[11] Patent Number: 6,103,882
[45] Date of Patent: Aug. 15, 2000

[54] METHOD OF PRODUCING A 19P2 LIGAND

[75] Inventors: Suenaga Masato, Hyogo; Moriya Takeo, Osaka; Tanaka Yoko, Kyoto; Nishimura Osamu, Hyogo, all of Japan

[73] Assignee: Takeda Chemical Industries, Ltd., Osaka, Japan

[21] Appl. No.: 09/105,678

[22] Filed: Jun. 26, 1998

[30] Foreign Application Priority Data

Jun. 27, 1997 [JP] Japan .................................. 9-172118

[51] Int. Cl.[7] .......................... A61K 38/01; A61K 38/24; A61K 38/00
[52] U.S. Cl. ........................ 530/407; 530/324; 530/399
[58] Field of Search .................................. 530/407, 324, 530/399; 435/252.33

[56] References Cited

FOREIGN PATENT DOCUMENTS

| 0 499 990 A2 | 8/1992 | European Pat. Off. . |
| 97/08317 | 3/1997 | WIPO . |
| 97/24436 | 7/1997 | WIPO . |

OTHER PUBLICATIONS

Nishimura et al. Synthesis of new peptides with prolactin-releasing activity by a combination of recombinant DNA technology and a cysteine-specific cyanylation reaction. Chem. Pharm. Bull. 46(9):1490–1492, Sep. 1998.

Copy of communication dated Nov. 27, 1998 with European Search Report re European Pat. Appln. No. 98111725.2–2106.

N. Koyama, et al. "A Novel Procedure For The Preparation of Biologically Active Recombinant Peptides Using a Cyanylation Reaction", Journal of Biotechnology 32 (1994), pp. 272–281.

Nobuyuki Koyama, et al. "A Novel Procedure for the Preparation of Biologically Active Recombinant Peptides Using a Cyanylation Reaction", Journal of Biotechnology, vol. 32, No. 2, 1994, pp. 273–281.

Shuji Hinuma, et al. "A Prolactin–Releasing Peptide in the Brain", Nature, vol. 393, May 21, 1998, pp. 272–276.

*Primary Examiner*—Bradley Sisson
*Assistant Examiner*—Devesh Srivastava
*Attorney, Agent, or Firm*—David G. Conlin; Robert L. Buchanan

[57] ABSTRACT

The method of the present invention is suitable for the commercial high-level production of a protein or peptide which can be used as a prophylactic and therapeutic drug for various diseases such as senile dementia, cerebrovascular dementia (dementia arising from cerebrovascular disorders), dementia associated with genealogical retroplastic diseases (e.g. Alzheimer's disease, Parkinson's disease, Pick's disease, Huntington's disease, etc.), dementia associated with infectious diseases (e.g. Creutzfeldt-Jakob's and other virus diseases), dementia associated with endocrine or metabolic disease or toxicosis (e.g. hypothyroidism, vitamin B12 deficiency, alcoholism, intoxication by drugs, metals, and organic compounds), dementia associated with tumorigenic diseases (e.g. brain tumor), dementia associated with traumatic diseases (e.g. chronic subarachnoidal hemorrhage), and other types of dementia, depression, hyperactive child syndrome (microencephalopathy), and disturbance of consciousness. Additionally, the ligand polypeptide of the present invention has prolactin secretion-stimulating and inhibiting activities.

3 Claims, 6 Drawing Sheets

```
                          9              18              27              36              45              54
5' TCC CGT GCT CAC CAG CAC TCC ATG GAA ATC CGT ACC CCG GAC ATC AAC CCG GCT ---
   --- --- --- --- --- --- --- --- --- --- --- --- --- --- --- --- --- --- ---
   Ser Arg Ala His Gln His Ser Met Glu Ile Arg Thr Pro Asp Ile Asn Pro Ala 63             72              81              90
   TGG TAC GCT GGT CGT GGT ATC CGT CCG GTT GGT CGT TTC 3'
   --- --- --- --- --- --- --- --- --- --- --- --- ---
   Trp Tyr Ala Gly Arg Gly Ile Arg Pro Val Gly Arg Phe
```

FIG. 2

```
                          9              18              27              36              45              54
5' TCC CGT GCT CAC CAG CAC TCC ATG GAA ACC CGT ACC CCG GAC ATC AAC CCG GCT ---
   --- --- --- --- --- --- --- --- --- --- --- --- --- --- --- --- --- --- ---
   Ser Arg Ala His Gln His Ser Met Glu Thr Arg Thr Pro Asp Ile Asn Pro Ala 63             72              81              90
   TGG TAC ACC GGT CGT GGT ATC CGT CCG GTT GGT CGT TTC 3'
   --- --- --- --- --- --- --- --- --- --- --- --- ---
   Trp Tyr Thr Gly Arg Gly Ile Arg Pro Val Gly Arg Phe
```

FIG. 3

```
5' TCC CGT ACC CAC CGT CAC TCC ATG GAA ATC CGT ACC CCG GAC ATC AAC CCG GCT
   ||| ||| ||| ||| ||| ||| ||| ||| ||| ||| ||| ||| ||| ||| ||| ||| ||| |||
   Ser Arg Thr His Arg His Ser Met Glu Ile Arg Thr Pro Asp Ile Asn Pro Ala
            9          18          27          36          45          54

TGG TAC GCT TCC CGT GGT ATC CGT GGT CCG GTT GGT CGT TTC 3'
   ||| ||| ||| ||| ||| ||| ||| ||| ||| ||| ||| ||| ||| |||
   Trp Tyr Ala Ser Arg Gly Ile Arg Gly Pro Val Gly Arg Phe
            63          72          81          90
```

FIG. 4

```
                                                                              *
  ┌TCTAGAAAGGAGATATACACTATGTCCCGTGCTCCACCAGCACTCCATGGAAATCCGTACCCCGGACATC
              #1                        │             #2
                                        │
  AGATC┤TTCCTCTATATGTGATACAGGGCACGAGGTGGTCGTGAGGTACC┤TTAGGCATGGGGCCTGTAG
              #4                                         #5
                                                                         126
  AACCCGGCTTGG┤TACGGCTGGTATCCGTTCCGGTTGGTCGTTTCTGCC┤CCGAG 3'
                   #3                                        5'
  TTGGGCCGAACCATGCCGACCATAGGCAGGCCAACCAGCCAAAGACGGGGCT┤C 5'
  *                          #6
```

FIG. 5

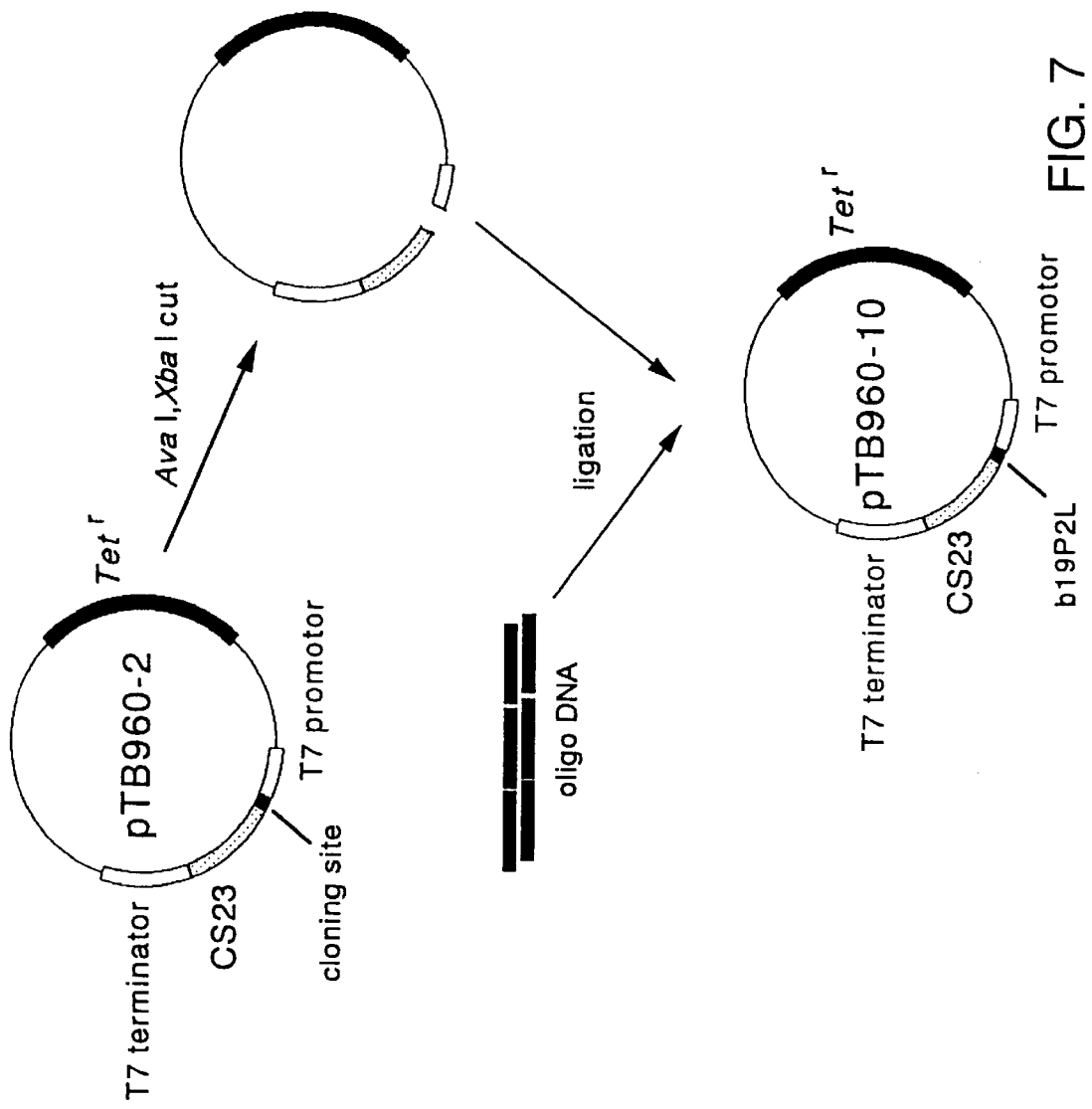

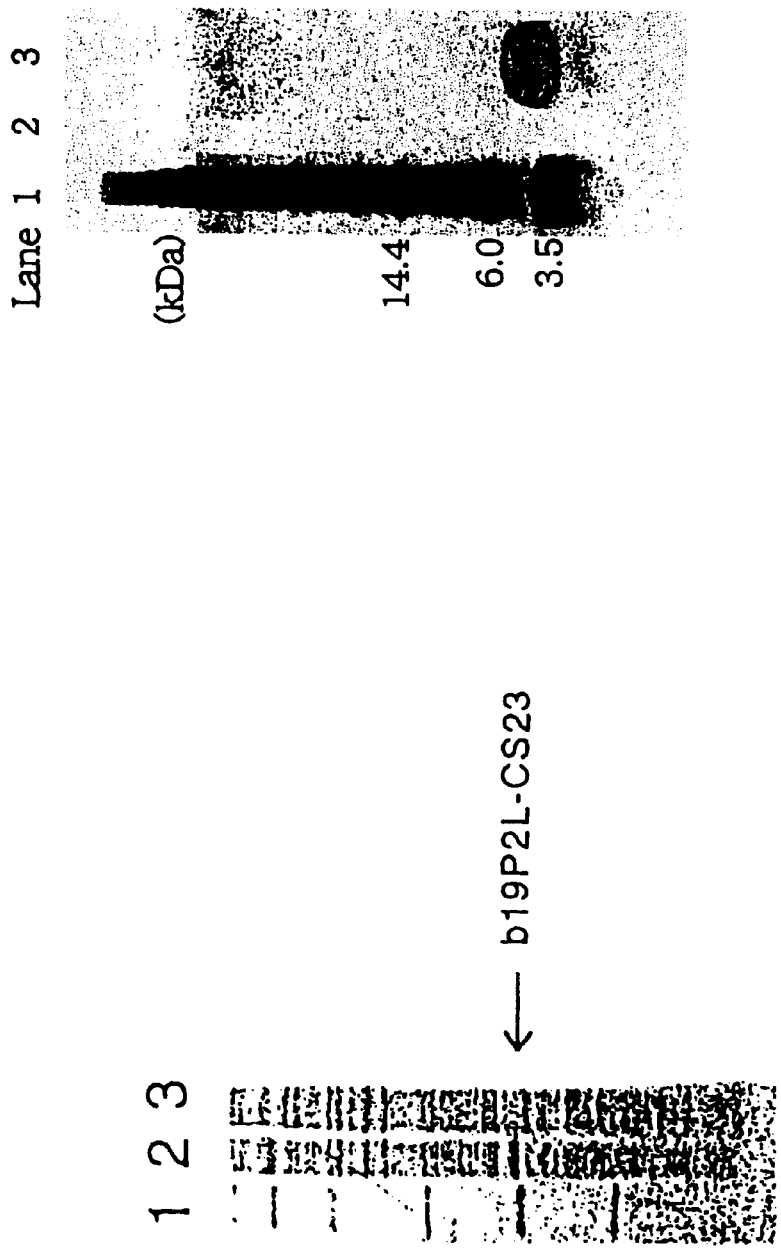

METHOD OF PRODUCING A 19P2 LIGAND

FIELD OF THE INVENTION

The present invention relates to a method of producing a 19P2 ligand (19P2L) or an amide thereof or a salt thereof which comprises preparing a fusion protein or peptide and subjecting said fusion protein or peptide to a peptide bond cleavage reaction.

BACKGROUND OF THE INVENTION

In the production of a protein or peptide by recombinant DNA technology, it is more or less common practice to have the protein or peptide expressed in the form of a fusion protein in view of the liability of the protein or peptide to be decomposed within living cells. For excision of the objective protein or peptide from the fusion protein, a chemical method for cleavage using cyanogen bromide (Itakura et al., Science, 198,1056, 1977) and an enzymatic method using factor Xa (Nagai et al., Methods in Enzymology, 153, 46, 1987) are known.

Furthermore, as a method for cleavage of a peptide bond in a protein, cleavage of the acylcysteine bond with 2-nitro-5-thiocyanobenzoic acid is known [Seikagaku Jikken Koza 1, Tanpakushitsu-no-Kagaku II (Biochemical Experiment Series 1, Protein Chemistry II), Japanese Society of Biochemistry (ed.), Tokyo Kagaku Dojin, 247–250, 1976]. However, there is no disclosure on the excision of an objective protein or peptide from a protein.

The prior art method which involves use of cyanogen bromide cannot be applied to the production of methionine-containing peptides, while the method involving use of factor Xa has drawbacks, for example in terms of excision yield.

Therefore, a demand exists for a technology by which an objective protein or peptide may be efficiently excised from a fusion protein or peptide.

The inventors of the present invention explored in earnest for a technology by which the novel bioactive peptide 19P2 ligand (19P2L, which is named as a "prolactin-releasing peptide (PrRP)" in Hinuma et al., Nature 393, 272–276, (1998)) may be produced with high efficiency and found that 19P2L can be efficiently produced by preparing a fusion protein or peptide comprising 19P2L fused to a protein or peptide having cysteine at its N-terminus and subjecting the fusion protein or peptide to a peptide bond cleavage reaction. The inventors did further research on the basis of the above finding and have accomplished the present invention.

SUMMARY OF THE INVENTION

The present invention, therefore, is directed to:
(1) A method of producing a 19P2L or an amide thereof or a salt thereof which comprises subjecting a fusion protein or peptide comprising the 19P2L fused to a protein or a peptide having a cysteine residue at the N-terminus to a reaction for cleavage of the peptide bond on the amino terminal side of the of the cysteine residue,
(2) A method of producing a 19P2L or an amide thereof or a salt thereof which comprises
① culturing a transformant harboring a vector containing a gene coding for a fusion protein or peptide comprising a 19P2L fused to a protein or a peptide having a cysteine residue at the N-terminus to express the fusion protein or peptide and
② subjecting the fusion protein or peptide expressed to a reaction for cleavage of the peptide bond on the amino-terminal side of the cysteine residue,
(3) The method of the above item (1) or (2) wherein the reaction for cleavage of the peptide bond on the amino-terminal side of the cysteine residue comprises ① cyanylation followed by ② ammonolysis or hydrolysis,
(4) The method of the above item (1) or (2) wherein the reaction for cleavage of the peptide bond on the amino-terminal side of the cysteine residue comprises ① cyanylation followed by ② ammonolysis to produce the amide of 19P2L,
(5) The method of the above item (1) or (2) wherein the 19P2L is bovine 19P2L (SEQ ID NO:7), rat 19P2L (SEQ ID NO:8), or human 19P2L (SEQ ID NO:9),
(6) A fusion protein or peptide comprising a 19P2L fused to a protein or a peptide having a cysteine residue at its N-terminus,
(7) A vector containing a gene coding for the fusion protein or peptide according to the above item (6), and
(8) A transformant harboring the vector according to the above item (7).

BRIEF DESCRIPTION OF THE DRAWINGS

FIG. 2 shows the amino acid sequence of bovine 19P2L.

FIG. 3 shows the amino acid sequence of rat 19P2L.

FIG. 4 shows the amino acid sequsnce of human 19P2L.

FIG. 5 shows the DNA fragment used in Example 1.

FIG. 7 shows the construction figure for plasmid pTB960-10 obtained in Example 1.

FIG. 8 shows the result of SDS-PAGE performed in Example 1.

FIG. 9 shows the result of SDS-PAGE performed in Example 6.

DESCRIPTION OF THE PREFERRED EMBODIMENTS

Figure 1:
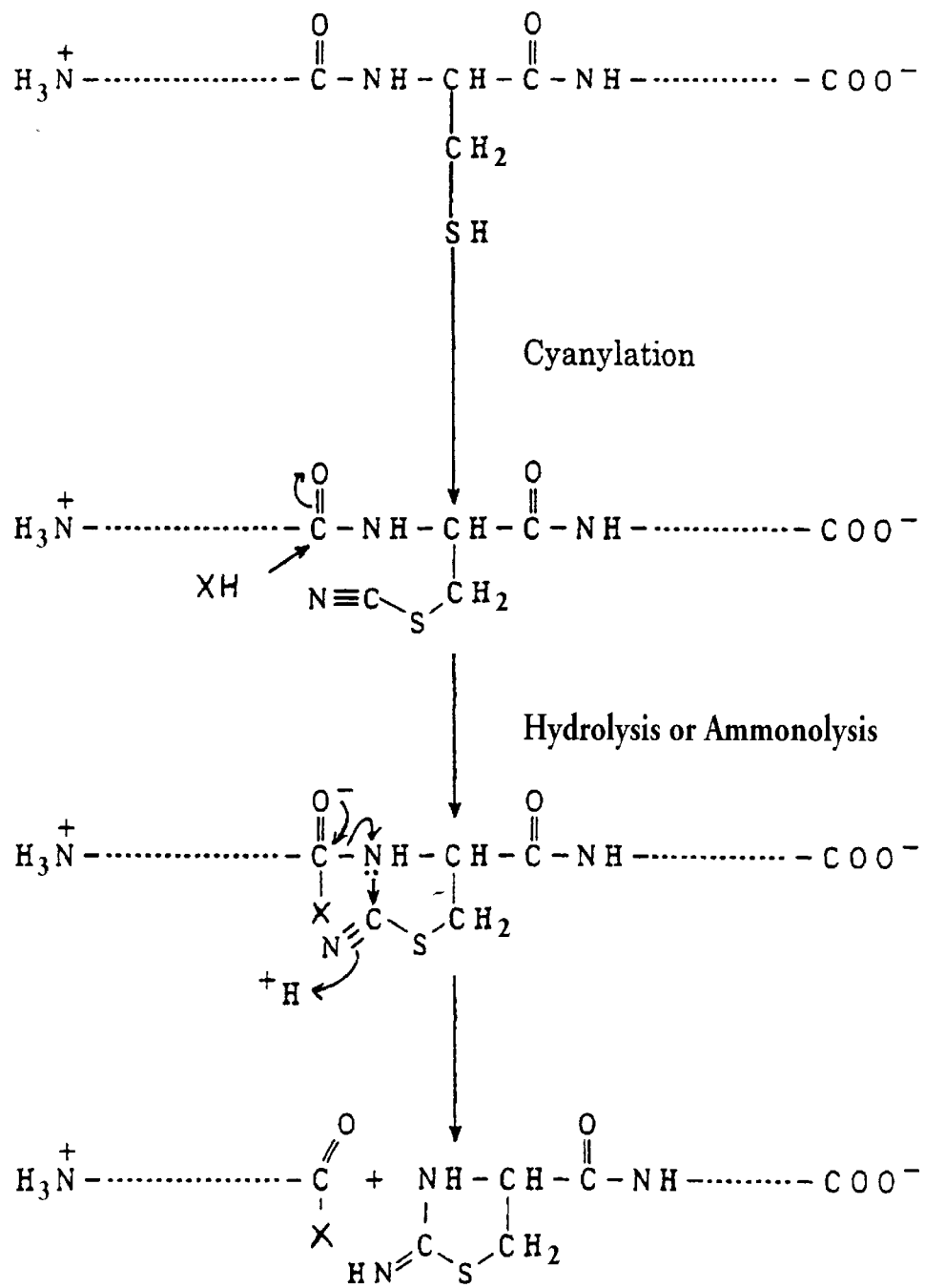
FIG. 1 shows the reaction mechanism of the reaction step in the present invention.

The 19P2L of the present invention includes but is not limited to the bovine 19P2L (b19P2L) (SEQ ID NO:7), rat 19P2L (r19P2L) (SEQ ID NO:8), and human 19P2L (h19P2L) (SEQ ID NO:9), all of which are described in Japanese Patent Application H8-348328 (International Publication Number WO97-24436) or an amide thereof or a salt thereof, or a substantial equivalent thereof.

For the product obtained by using the method of this invention, an amide of 19P2L, wherein the phenylalanine of the C-terminus of 19P2L is amidated to form phenylalaninamide, is preferable.

The term "substantial equivalent" means the nature of the receptor-binding activity, signal transduction activity and the like is equivalent. Thus, it is allowable that even differences among grades such as the strength of receptor binding activity and the molecular weight of the protein or peptide are present.

For example, in addition to the protein comprising the amino acid sequence of SEQ ID NO:7, SEQ ID NO:8 or SEQ ID NO:9, 19P2L of the present invention includes the protein or peptide comprising an amino acid sequence having a homology of about 50–99.9%, preferably 70–99.9%, more preferably 80–99.9% and especially preferably 90–99.9% to the amino acid sequence of SEQ ID NO:7, SEQ ID NO:8 or SEQ ID NO:9 and having qualitatively substantially equivalent activity to the protein or peptide comprising the amino acid sequence of SEQ ID NO:

7, SEQ ID NO:8 or SEQ ID NO:9, provided that the above protein or peptide having the substantially equivalent activity to the protein comprising the amino acid sequence of SEQ ID NO: 7, SEQ ID NO: 8 or SEQ ID NO:9 does not have any cystein residues in their amino acid sequence(s).

To be more specific, the substantially equivalent protein or peptide of 19P2L of the present invention includes the protein or peptide comprising the amino acid sequence of SEQ ID NO:73 (SEQ ID NO:28 of the present specification, wherein the 10th Xaa shows Ala or Thr, the 11th Xaa shows Gly or Ser, the 21st Xaa shows OH, Gly or Gly-Arg) described in Japanese Patent Application H8-348328 (International Publication Number WO9724436).

In addition, the substantially equivalent protein or peptide of 19P2L of the present invention includes (1) the protein or peptide which comprises a substantially equivalent protein or peptide such as protein or peptide wherein 1 to 15, preferably 1 to 10, and more preferably 1 to 5 amino acid residues are deleted from the amino acid sequence of SEQ ID NO:7, SEQ ID NO:8 or SEQ ID NO:9, (2) the protein or peptide wherein 1 to 80, preferably 1 to 50, more preferably 1 to 10 amino acid residues are added to the amino acid sequence of SEQ ID NO:7, SEQ ID NO:8 or SEQ ID NO:9, or (3) the protein or peptide wherein 1 to 15, preferably 1 to 10, more preferably 1 to 5 amino acid residues are substituted with one or more other amino acid residues.

The amino acid sequence of SEQ ID NO:7, SEQ ID NO:8 or SEQ ID NO:9 comprises SEQ ID NO:3, 4, 5, 6, 7, 8, 9, 10, 47, 48, 49, 50, 51, 52, 61,62, 63, 64, 65 or 66described in Japanese Patent Application H8-348328 (International Publication Number WO97-24436), each of these SEQ ID Nos are correspond to SEQ ID NO:29 to 48 shown in this specification, respectively.

Furthermore, 19P2L of this invention includes those wherein the N-terminal side of Gln is cleaved in vivo to form pyroglutamyl peptide.

The protein or peptides, including 19P2L, described in this specification, the left ends are the N-terminus (amino terminus) and the right end is the C-terminus (carboxyl terminus) according to the convention of the peptide indication.

While the C-terminus of the polypeptide of SEQ ID NO:7, SEQ ID NO:8 or SEQ ID NO:9 is usually carboxyl (—COOH) or carboxylato (—COO⁻), it may be amide (—CONH$_2$), alkylamide (—CONHR) or ester (—COOR) form. The ester and alkylamide residue R includes a C$_{1-6}$ alkyl group such as methyl, ethyl, n-propyl, isopropyl, n-butyl, etc., aC$_{3-8}$cycloalkyl group such as cyclopentyl, cyclohexyl, etc., a C$_{6-12}$ aryl group such as phenyl, α-naphthyl, etc., and a C$_{7-14}$ aralkyl group such as a phenyl-C$_{1-2}$ alkyl group, e.g. benzyl, phenethyl, benzhydryl, etc. or ana-naphthyl-C$_{1-2}$ alkyl, e.g. α-naphthylmethyl etc. In addition, the ester may be a pivaloyloxymethyl ester which is broadly used for oral administration. When the polypeptide of SEQ ID NO:7, SEQ ID NO:8 or SEQ ID NO:9 has a carboxyl or carboxylato group in any position other than the C-terminus, the corresponding amide is also included in the concept of the protein or peptide of the present invention.

The salt of the protein or peptide, including 19P2L, of the present invention includes salts with physiologically acceptable bases, e.g. alkali metals or acids such as organic or inorganic acids, and is preferably a physiologically acceptable acid addition salt. Examples of such salts are salts thereof with inorganic acids, e.g. hydrochloric acid, phosphoric acid, hydrobromic acid or sulfuric acid, etc. and salts thereof with organic acids, e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.

The protein or peptide having cysteine at its N-terminus for use in the method of the invention is not particularly restricted. A protein or peptide not having cysteine at its N-terminus may also be used after modification so that it will have cysteine at its N-terminus by an ordinally method.

The molecular weight of the protein or peptide having cysteine at its N-terminus is preferably 100 to 100000 and more preferably 300 to 50000. Furthermore, the protein or peptide having cysteine at its N-terminus is preferably a protein or peptide containing 1 to 1000 amino acid residues and more preferably one containing 3 to 500 amino acid residues.

The protein or peptide mentioned above includes a variety of proteins or peptides which have cysteine at the N-terminus, such as growth factors, e.g. interferons, interleukins, fibroblast growth factors (aFGF, bFGF, etc.), etc., enzyme proteins such as (pro)urokinases, lymphotoxin, tumor necrosis factor (TNF), β-galactosidase, etc., storage proteins, streptavidin, protein A, protein G, tissue plasminogen activator (TPA), and their muteins and fragments.

Among them, fibroblast growth factors (aFGF, bFGF, etc.) or their muteins (e.g. bFGF CS23 mutein(EP-A 499990)) are preferablly used.

The bFGF CS23 mutein has the amino acid sequence represented as follows:
NH$_2$-Pro-Ala-Leu-Pro-Glu-Asp-Gly-Gly-Ser-Gly-Ala-Phe-
Pro-Pro-Gly-His-Phe-Lys-Asp-Pro-Lys-Arg-Leu-Tyr-
Cys-Lys-Asn-Gly-Gly-Phe-Phe-Leu-Arg-Ile-His-Pro-
Asp-Gly-Arg-Val-Asp-Gly-Val-Arg-Glu-Lys-Ser-Asp-
Pro-His-Ile-Lys-Leu-Gln-Leu-Gln-Ala-Glu-Glu-Arg-
Gly-Val-Val-Ser-Ile-Lys-Gly-Val-Ser-Ala-Asn-Arg-Tyr-
Leu-Ala-Met-Lys-Glu-Asp-Gly-Arg-Leu-Leu-Ala-Ser-
Lys-Ser-Val-Thr-Asp-Glu-Cys-Phe-Phe-Phe-Glu-Arg-
Leu-Glu-Ser-Asn-Asn-Tyr-Asn-Thr-Tyr-Arg-Ser-Arg-
Lys-Tyr-Thr-Ser-Trp-Tyr-Val-Ala-Leu-Lys-Arg-Thr-Gly-
Gln-Tyr-Lys-Leu-Gly-Ser-Lys-Thr-Gly-Pro-Gly-Gln-
Lys-Ala-Ile-Leu-Phe-Leu-Pro-Met-Ser-Ala-Lys-Ser-
COOH (SEQ ID NO.49)

Referring to the above-mentioned gene coding for a fusion protein (inclusive of a fusion peptide) for use in the method of the invention,
(1) its complete nucleotide sequence may be chemically synthesized or (2) the gene may be constructed by arranging a nucleotide sequence coding for cysteine on the N-terminal side of the nucleotide sequence coding for the protein and further arranging a nucleotide sequence coding for 19P2L on its N-terminal side. Moreover, (3) for the production of a fragment of said peptide, the gene can be constructed by substituting cysteine for the amino acid residue immediately downstream of the objective fragment by a suitable technique such as site-directed mutagenesis.

In the production method (1) mentioned above, the objective gene can be constructed by carrying out the necessary synthesis, in one step when the sequence is short, or in divided steps when the sequence is long, by the known phosphamidide method, phosphoric acid triester or diester method, hydrogenphosphonate method, or the like and, in the latter case, ligating the synthesized fragments using T4DNA ligase.

The production method (2) mentioned above may for example be carried out as follows. The gene coding for the C-terminal protein is prepared by digesting a chromosome with suitable restriction enzymes and ligating the digest to a vector. As an alternative, a cDNA is prepared. Then, it is modified by cleavage with a restriction enzyme so that the N-terminus will be cysteine, or by conjugating a synthetic DNA to the 5'-end of the gene coding for the total protein or a fragment thereof so that the N-terminus will be cysteine. Then, the gene (which may be one chemically synthesized or cloned from a living tissue) coding for the objective protein is linked to its 5'-end.

The thus-obtained gene coding for the fused protein may for example be the DNA of the formula:

```
TCCCGTGCTCACCAGCACTCCATGGAAATCCGTACCCCGGACATCAACCCGGCTTGG    (1)

TACGCTGGTCGTGGTATCCGTCCGGTTGGTCGTTTC-TGC or TGT-R
(e.g. the DNAS of SEQ ID NO:1 and 2);

TCCCGTGCTCACCAGCACTCCATGGAAACCCGTACCCCGGACATCAACCCGGCTTGG    (2)

TACACCGGTCGTGGTATCCGTCCGGTTGGTCGTTTC-TGC or TGT-R
(e.g. the DNAs of SEQ ID NO:3 and 4); or

TCCCGTACCCACCGTCACTCCATGGAAATCCGTACCCCGGACATCAACCCGGCTTGG    (3)

TACGCTTCCCGTGGTATCCGTCCGGTTGGTCGTTTC-TGC or TGT-R
(e.g. the DNAs of SEQ ID NO:5 and 6);

[wherein R represents a nucleotide sequence consisting of

CCCGAGGATGGCGGCAGCGGCGCCTTCCCGCCCGGCCACTTCAAGGACCCCAAGCGG

CTGTACTGCAAAAACGGGGGCTTCTTCCTGCGCATCCACCCCGACGGCCGAGTTGAC

GGGGTCCGGGAGAAGAGCGACCCTCACATCAAGCTACAACTTCAAGCAGAAGAGAGA

GGAGTTGTGTCTATCAAAGGAGTGAGCGCTAATCGTTACCTGGCTATGAAGGAAGAT

GGAAGATTACTAGCTTCTAAGTCTGTTACGGATGAGTGTTTCTTTTTTGAACGATTG

GAATCTAATAACTACAATACTTACCGGTCAAGGAAATACACCAGTTGGTATGTGGCA

CTGAAACGAACTGGGCAGTATAAACTTGGATCCAAAACAGGACCTGGGCAGAAAGCT

ATACTTTTTCTTCCAATGTCTGCTAAGAGCTGC (a fragment of hbFGF mutein CS23)]
```

In the above formulas, (1), (2), and (3) indicate that the nucleotide sequence represented by R is coupled, through the nucleotide sequence coding for cysteine, to the DNA nucleotide sequences coding for bovine, rat, and human 19P2Ls (SEQ ID NO:7, 8, and 9), respectively.

A DNA (plasmid) having ATG at 5'-end, a region coding for said fusion protein downstream thereof, and a translation termination codon further downstreams can be produced by processing the known cDNA of said protein which has been chemically synthesized or prepared by recombinant DNA technology or the protein DNA of the chromosomal origin.

The gene coding for the fusion protein or peptide comprising 19P2L fused to a protein or peptide having cysteine at its N-terminus according to the invention can be converted to a gene coding for the objective mutein by the conventional DNA technology, for example site-directed mutagenesis.

The technique of site-directed mutagenesis is well known as described in Lather, R. F. & Lecoq, J. P., Genetic Engineering, 31–50, 1983 (Academic Press); the technique of oligonucleotide-directed mutagenesis is described in Smith, M. & Gillam, S., Genetic Engineering, Principles and Methods, Plenum Press, 3, 1–32, 1981.

The plasmid which can be used as a vector in the production of a plasmid having a DNA containing a region coding for said fusion protein includes but is not limited to E. coli-derived pBR322 [Gene, 2, 95 (1977)], pBR313 [Gene, 2, 75 (1977)], pBR324, pBR325 [Gene, 4, 124 (1978)], pBR327, pBR328 [Gene, 9, 287 (1980)], pBR329 [Gene, 17, 79 (1982)], pKY2289 [Gene, 3, 1 (1978)], pKY2700 [Journal of the Japanese Biochemical Society, 52, 770 (1980)], pACYC177, pACYC184 [Journal of Bacteriology, 134, 1141 (1978)], pRK248, pRK646, pDF [Methods in Enzymology, 68, 268 (1979)], and pUC18 and pUC19 [Yanisch-Perron et al., Gene, 33, 103 (1985). There can also be mentioned bacteriophage vectors, e.g. λ phage vectors such as λgt·λC[Proc. Nat. Acad. Sci. U.S.A. 71, 4579(1974)], λgt·λB [Proc. Nat. Acad. Sci. U.S.A. 72, 3461 (1975)], λDam [Gene, 1,255(1977)], Charonvector [Science, 196, 161(1977); Journal of Virology, 29, 555 (1979)] and mp18 and mp19 [Yanisch-Perron et al., Gene, 33, 103 (1985)] vectors in the mp series using filamentous phages.

The above-mentioned DNA preferably has a promoter region upstream of ATG and this promoter may be any suitable promoter for the host used in the construction of a transformant.

For *Escherichia coli*, for instance, trp promoter, lac promoter, rec A promoter, λPL promoter, lpp promoter, T7 promoter, etc. can be used. For *Bacillus subtilis*, SPO1 promoter, SPO2 promoter, penP promoter, etc. and for *Saccharomyces cerevisiae*, PHO5 promoter, PGK promoter, GAP promoter, ADH promoter, etc. can be used. For animal cells, SV40-derived promoters can be mentioned. Where necessary, the Shine-Dalgarno (SD) sequence may be inserted downstream of the promoter.

When a T7 series promoter is used, any of promoters found on T7DNA [J. L. Oakley et al., Proc, Natl, Acad. Sci, U.S.A. 74, 4266–4270 (1977); M. D. Rosa, Cell, 16, 815–825 (1979); N. Panayotatos et al., Nature, 280, 35 (1979); J. J. Dunn et al., J. Mol. Biol., 166, 477–535 (1983)]

can be used, although φ10 promoter [A. H. Rosenberg et al., Gene, 56,125–135(1987)] is preferred.

As the transcription terminator, a terminator operable in the *E. coli* system, preferably Tφ terminator [F. W. Studier et al., J. Mol. Biol., 189, 113–130 (1986)] is used.

As the T7RNA polymerase gene, T7 gene 1 [F. W. Studier et al., J. Mol. Biol., 189, 113–130 (1986)] can be mentioned.

The vector is preferably constructed by inserting the T7 promoter and T7 terminator in the vector described hereinbefore. As examples of such vector, pET-1, pET-2, pET-3, pET-4, pET-5 [A. H. Rosenberg, Gene, 56, 125–135 (1987)] and pTB960-2 [EP-A-499990] can be mentioned, although pTB960-2 is preferred.

The transformant of the invention can be constructed by transforming a host with the above-prepared expression plasmid by a per se known technique [e.g. Cohen, S. N. et al., Pro. Natl. Acad. Sci. U.S.A., 69, 2110 (1972)].

The host to be transformed includes bacteria of the genus Escherichia, bacteria of the genus Bacillus, yeasts, and animal cells, among others.

The above-mentioned bacteria of the genus Escherichia include *Escherichia coli* K12DH1 [Proc. Natl. Acad. Sci. U.S.A., 60, 160 (1968)], JM-103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], N4830 [Cell, 25, 713 (1981)], and K-12 MM294 [Proc. Natl. Acad. Sci. U.S.A., 73, 4174 (1976)] BL-21, among others.

The above-mentioned bacteria of the genus Bacillus include but are not limited to strains of *Bacillus subtilis* such as Bacillus subtilis MI114 [Gene, 24, 255 (1983)] and 207–21 [Journal of Biochemistry, 95, 87 (1984)].

The above-mentioned yeasts include but are not limited to strains of *Saccharomyces cerevisiae* such as *Saccharomyces cerevisiae* AH22 [Proc. Natl. Acid. Sci. U.S.A., 75, 1929 (1978)], XSB52-23C [Proc. Natl. Acid. Sci. U.S.A., 77, 2173 (1980)], BH-641A [ATCC 28339], 20B-12 [Genetics, 85, 23 (1976)], and GM3C-2 [Proc. Natl. Acid. Sci. U.S.A., 78, 2258 (1981)].

The animal cells include but are not limited to monkey COS-7 [Cell, 23, 175 (1981)], Vero [Japanese Journal of Clinics, 21, 1209 (1963)], Chinese hamster CHO [J. Exp. Med., 108, 945 (1985)], mouse L [J. Nat. Cancer Inst., 4, 165 (1943)], human FL [Proc. Sco. Etp. Biol. Med., 94, 532 (1957)], and hamster C cell lines.

When a T7 series promoter is used, the host for transformation which can be used is any *E. coli* strain that can be made available by integration with T7 RNA polymerase gene (T7 gene 1) [F. W. Studier et al., J. Mol. Biol., 189, 113-130 (1986)], such as MM294, DH-1, C600, JM109, BL21, etc. or any *E. coli* strain that can be made available by integration with T7 RNA polymerase gene (T7 gene 1) and another plasmid. Preferred are MM294 and BL21 strains in which the λ phage integrated with T7 gene 1 is in lysogenic state. In this case, as the promoter of T7 gene 1, lac promoter whose expression can be induced with isopropyl-1-thio-β-D-galactopyranoside (sometimes abbreviated as IPTG) is employed.

Transformation of a Bacillus strain as the host can be carried out in accordance with the known technology, for example the method described in Molecular and General Genetics, 168, 111 (1979).

Transformation of a yeast as the host can be carried out by the known technology, for example the method described in Proc. Natl. Acad. Sci. U.S.A., 75, 1929 (1978).

Transformation of an animal cell line as the host can also be carried out by the known technology, for example the method described in Virology, 52, 456 (1973).

The fusion protein or peptide can be produced by culturing the above transformant in a medium and harvesting the fusion protein produced.

The pH of the medium is preferably about 6 to 8.

The preferred medium for culture of strains of the genus Escherichia includes but is not limited to M9 medium supplemented with glucose and casamino acids [Miller, Journal of Experiments in Molecular Genetics, 431–433; Cold Spring Harbor Laboratory, New York (1972)]. Here, to let the promoter function with improved efficiency, a reagent such as 3 β-indolyl-acrylic acid or isopropyl-β D-thiogalactopyranoside can be optionally added.

When the host is a strain of the genus Escherichia, it can be cultured generally at about 15 to 43° C. for about 3 to 24 hours, optionally under aeration and stirring.

When the host is a Bacillus strain, it can be cultured generally at about 30 to 40° C. for about 6 to 24 hours, optionally under aeration and stirring.

The transformant obtained by using a yeast as the host can be cultured in a medium such as Burkholder minimal medium [Bostian, K. L. et al., Proc. Natl. Acad. Sci. U.S.A., 77, 4505 (1989)]. The pH of the medium is preferably adjusted to about 5 to 8. The cultivation is generally conducted at about 20 to 35° C. for about 24 to 27 hours, optionally under aeration and stirring.

The transformant obtained by using animal cells as the host can be cultured in a medium such as 0.2 to 20% (approx.), preferably 5 to 20% (approx.), fetal calf serum-containing MEM [Science, 122, 501 (1952)], DME medium [Virology, 8, 396 (1959)], RPMI 1640 medium [The Journal of the American Medical Association, 199, 519 (1967)], or 199 medium [Proceedings of the Society for Biological Medicine, 73, 1 (1950)]. The preferred pH of the medium is about 6 to 8. The cultivation is generally conducted at 30 to 40° C. for about 15 to 60 hours, optionally under aeration and stirring.

The fusion protein or peptide can be produced by growing said transformant to let it elaborate and accumulate the objective fusion protein in the culture broth and harvesting it from the broth.

The medium that can be used for this purpose includes M9 medium supplemented with glucose and casamino acids [Miller, J., Experiments in Molecular Genetics, 431–433, Cold Spring Harbor Laboratory, New York (1972)], 2XYT medium [Messing, Methods in Enzymology, 101, 20 (1983)], and LB medium, among others.

The cultivation is generally conducted at about 15 to 43° C. for about 3 to 24 hours, optionally under aeration and stirring.

When a transformant harboring the α cIts repressor- and λ $P_L$ promoter-containing expression vector is used, the cultivation is conducted at a temperature of about 15 to 36° C., preferably about 30 to 36° C., and the inactivation of the λ cits repressor is preferably carried out at about 37 to 42° C. In order that the recA promoter may function efficiently, that is to say the recA gene expression-suppressive function may be attenuated, either a reagent such as mitomycin C or nalidixic acid is added, UV irradiation is carried out, or the pH of the culture medium is changed to the alkaline side.

Referring to the case in which a T7 series promoter is employed, (1) when the T7 gene (RNA polymerase gene) linked downstream of lac promoter is to be expressed, IPTG or the like is added or (2) when the T7 gene (RNA polymerase gene) linked downstream of λ $P_L$ promoter is to be expressed, the incubation temperature is increased, for instance, whereby the T7 promoter is activated by the T7 phage RNA polymerase 1 produced.

After cultivation, the cells are harvested by a known procedure, suspended in a buffer, disrupted by treatment with a protein denaturing agent, sonication, enzymatic treatment with, for example, lysozyme, glass beads treatment, treatment with a French press, freeze-thaw, or the like, and centrifuged or otherwise processed in a known manner to recover a supernatant.

From the supernatant thus obtained, the fusion protein or peptide can be isolated by the generally known protein purification technology. Thus, for example, gel permeation chromatography, ion exchange chromatography, adsorption chromatography, high-performance liquid chromatography, affinity chromatography, hydrophobic chromatography, and electrophoresis are utilized in a suitable combination. There are cases in which methionine derived from the translation initiation codon has been added to the N-terminus of said fusion protein or peptide. This fusion protein or peptide may be submitted to the following reaction step without being purified or in a partially purified state.

The fusion protein or peptide thus obtained is then submitted to a reaction for cleavage of the peptide bond on the amino-terminal side of the cysteine residue.

This cleavage reaction may, for example, comprise cyanylation followed by ammonolysis or hydrolysis.

The cyanylation reaction mentioned above is carried out by permitting an S-cyanating agent to act upon the substrate compound.

The S-cyanating agent may for example be 2-nitro-5-thiocyanobenzoic acid (NTCB), 1-cyano-4-dimethylaminopyridinium salt (DMAP-CN), or CN$^-$ ion. The necessary amount of said S-cyanating agent is about 2 to 50 equivalents, preferably 5 to 10 equivalents, with respect to the total of thiol groups available.

The reaction temperature may be any temperature between about 0° and about 80° C., preferably about 0 to 50° C. The solvent may be any buffer solution that does not react with the cyanating agent and includes Tris-hydrochloric acid buffer, Tris-acetate buffer, phosphate buffer, and borate buffer, among other buffers. An organic solvent may be present unless it is reactive with the cyanating agent.

This reaction is preferably carried out in a pH range of 1 to 12. Particularly when NTCB is used, the range of pH 7 to 10 is preferred and when DMAP-CN is used, the range of pH 2 to 7 is preferred for avoiding an S—S exchange reaction. In the reaction system, a denaturing agent such as guanidine hydrochloride may be present.

The ammonolysis or hydrolysis reaction may for example be carried out using an alkali.

This alkali treatment can be carried out by adjusting an aqueous solution of the substrate compound to pH 7 to 14.

This pH adjustment is carried out by adding a suitable amount of an aqueous solution of ammonia, sodium hydroxide, an amino compound, Trizma base [tris(hydroxymethyl)aminomethane], disodium hydrogenphosphate, potassium hydroxide, barium hydroxide, or the like to an aqueous solution of the substrate compound. The amino compound mentioned above may for example be a compound of the formula R$^1$—(N—R$^2$)—H.

In the above formula, R$^1$ and R$^2$ may be the same or different and each represents
(i) hydrogen,
(ii) $C_{1-20}$ alkyl, $C_{3-8}$ cycloalkyl, $C_{6-14}$ aryl, or $C_{6-14}$ aryl-$C_{1-3}$ alkyl (each of which may be unsubstituted or substituted by 1–3 amino, hydroxy, or other groups on carbon),
(iii) amino which may be substituted, or
(iv) hydroxy or $C_{1-6}$ alkoxy.

The above-mentioned $C_{1-20}$ alkyl includes methyl, ethyl, propyl, isopropyl, butyl, sec-butyl, pentyl, isopentyl, neopentyl, 1-ethylpentyl, hexyl, isohexyl, heptyl, octyl, nonyl, decyl, undecyl, dodecyl, tetradecyl, pentadecyl, hexadecyl, heptadecyl, octadecyl, nonadecyl, and eicosyl.

The $C_{3-8}$ cycloalkyl includes but is not limited to cyclopropyl, cyclobutyl, cyclopentyl, cyclohexyl, cycloheptyl, and cyclooctyl.

The $C_{6-14}$ aryl includes but is not limited to phenyl, naphthyl, anthryl, phenanthryl, and acenaphthylenyl.

The $C_{6-14}$ aryl-$C_{1-3}$ alkyl includes but is not limited to benzyl, phenethyl, 3-phenylpropyl, (1-naphthyl)methyl, and (2-naphthyl)methyl.

The $C_{1-6}$ alkoxy includes methoxy, ethoxy, propoxy, butoxy, pentyloxy, and hexyloxy.

The substituent group for said (iii) amino which may be substituted includes but is not limited to amino acids and peptides of 2 to 10 amino acid residues.

The amino acids mentioned just above may be whichever of the L- and D-forms and include but are not limited to Ala, Arg, Asp, Asn, Glu, Gln, Gly, His, Ile, Met, Leu, Phe, Pro, Ser, Thr, Trp, Tyr, and Val.

The peptides include but are not limited to H-D-Leu-Leu-Arg-Pro-NH-C$_2$H$_5$ and H-Val-Ala-Leu-D-Ala-Ala-Pro-Leu-Ala-Pro-Arg-OH.

The concentration of the alkaline solution for use in the above reaction may for example be about 0.01 to 15 N, preferably about 0.1 to 3 N, for ammonia or an amino compound, about 0.01 to 2 N, preferably about 0.1 to 1 N, for sodium hydroxide, about 1 mM to 1 M, preferably about 20 mM to 200 mM, for Trizma base, about 1 mM to 1 M, preferably about 10 mM to 100 mM, for disodium hydrogenphosphate, about 0.01 to 4 N, preferably about 0.1 to 2 N, for potassium hydroxide, or about 0.01 to 0.2 M, preferably about 0.1 to 0.2 M, for barium hydroxide. The reaction temperature may be any temperature between about 0° C. and about 80° C. and preferably about 0° C. to 5° C.

The preferred reaction time is about 1 to 60 minutes, particularly about 15 to 30 minutes, for cyanylation, about minutes to 100 hours, particularly about 10 minutes to hours, for hydrolysis, or about 5 minutes to 24 hours, particularly about 10 to 180 minutes, for ammonolysis.

The above cyanylation and ammonolysis or hydrolysis appear to proceed as illustrated in FIG. 1. In FIG. 1, X represents R$^1$—(NR$^2$)— (wherein the respective symbols have the same meanings as defined hereinbefore) or OH.

When ammonia or an amino compound is used in this reaction, the corresponding amide is produced.

The excised protein or peptide can be isolated by the conventional method for protein or peptide purification. For example, gel permeation chromatography, ion exchange chromatography, high-performance liquid chromatography, affinity chromatography, hydrophobic chromatography, thin-layer chromatography, and electrophoresis can be selectively used in a suitable combination. While the objective protein or peptide thus obtained may have methionine derived from the initiation codon at its N-terminus, this N-terminal methionine can be eliminated by, for example, the method described in Japanese Patent Application H9-156777, which comprises reacting the protein or peptide with an a diketone such as glyoxylic acid (preferably in the presence of a transition metal ion, e.g. copper sulfate, and a base, e.g. pyridine) and hydrolyzing the reaction product with a diamine such as o-phenylenediamine.

Where necessary, the objective protein or peptide, including 19P2L, thus obtained can be provided as lyophilized powders. In the lyophilizing procedure, there may be added a stabilizer such as sorbitol, mannitol, dextrose, maltose, trehalose, or glycerol.

Bovine 19P2L (the amino acid sequence of which is presented in FIG. 2; SEQ ID NO:7), rat 19P2L (the amino acid sequence of which is presented in FIG. 3; SEQ ID NO:8), and human 19P2L (the amino acid sequence of which is presented in FIG. 3; SEQ ID NO:9) as produced by the method of the invention are ligands of pituitary G protein-coupled receptors and those ligands which may be found to be their agonists or antagonists by assay systems using the ligands are expected to find application as drugs.

The protein or peptide (19P2L) or an amide thereof or a salt thereof obtained by the method of the invention can be admixed with a known physiologically acceptable carrier such as sterile water, human serum albumin (HAS), physiological saline, or the like and administered parenterally or locally. For example, a daily dose of about 0.01 mg to 50 mg, preferably about 0.1 mg to 10 mg, per patient can be administered parenterally, e.g. by intravenous or intramuscular injection.

Pharmaceutical compositions containing the protein or peptide (19P2L) produced by the method of the invention may contain other physiologically acceptable ingredients such as salts, diluents, adjuvants, other carriers, buffers, binders, surfactants, and preservatives. Parenteral dosage forms may for example be ampules each containing a sterile aqueous solution or suspension of the protein or peptide (19P2L) in a physiologically acceptable medium or vials each containing sterile powders (usually obtained by lyophilization of a solution of the protein or peptide (19P2L)) which can be extemporaneously reconstituted with a physiologically acceptable diluent.

The protein or peptide (19P2L) or an amide thereof or a salt thereof produced by the method of the invention can be used as a therapeutic and prophylactic drug for senile dementia, cerebrovascular dementia, dementia associated with genealogical retroplastic diseases (e.g. Alzheimer's disease, Parkinson's disease, Pick's disease, Huntington's disease, etc.), dementia associated with infectious diseases (e.g. Creutzfeldt-Jakob's and other slow virus diseases), dementia associated with endocrine or metabolic disease or toxicosis (e.g. hypothyroidism, vitamin B12 deficiency, alcoholism, intoxication by drugs, metals, organic compounds, etc.), dementia associated with tumorigenic diseases (e.g. brain tumor), dementia associated with traumatic diseases (e.g. chronic subarachnoidal hemorrhage), and other types of dementia, depression, hyperactive child syndrome (microencephalopathy), disturbance of consciousness, anxiety syndrome, schizophrenia, phobia, growth hormone secretion disorder (gigantism, acromegaly, etc.), hyperphagia, polyphagia, hypercholesterolemia, hyperglyceridemia, hyperlipemia, hyperprolactinemia, diabetic complications such as diabetic nephropathy, diabetic neuropathy, diabetic retinopathy, etc., diabetes mellitus, cancer (e.g. mammary cancer, lymphatic leukemia, cystic cancer, ovary cancer, carcinoma of the prostate, etc.), pancreatitis, kidney diseases (e.g. chronic renal failure, nephritis, etc.), Turner's syndrome, neurosis, rheumatoid arthritis, spinal injury, transient cerebral ischemia, amyotrophic lateral sclerosis, acute myocardial infarction, spinocerebellar degeneration, bone fracture, wound, atopic dermatitis, osteoporosis, asthma, epilepsy, infertility, hypogalactia, and other diseases. In addition, it can be used as a postoperative nutriture improving agent or a vasopressor.

The ligand polypeptide of the present invention has prolactin secretion-stimulating and -inhibiting activities. Thus, the ligand polypeptide of the invention has prolactin secretion-stimulating activity and, therefore, finds application as a prophylactic and therapeutic drug for various diseases associated with prolactin hyposecretion. On the other hand, the ligand polypeptide of the invention has a high affinity for the receptor proteins and, therefore, when used in an increased dose, causes desensitization for prolactin secretion, thus exhibiting prolactin secretion-inhibiting activity. In this sense, it can be used as a prophylactic and therapeutic drug for various diseases associated with prolactin hypersecretion.

Futhermore, the 19P2L or an amide thereof or a salt therof of the invention can be used with advantage as a prolactin secretion-stimulating agent for the prevention and treatment of certain diseases associated with prolactin secretion, such as hypoovarianism, seminal vesicle hypoplasia, osteoporosis, menopausal syndrome, agalactorrhea, hypothyroidism, and renal failure.

On the other hand, the 19P2L or an amide thereof or a salt therof of the invention can be used with advantage as a prolactin secretion-inhibitory agent in the prevention and treatment of certain diseases associated with prolactin secretion, such as hyperprolactinemia, pituitary adenoma, tumor of diencephalon, emmeniopathy, stress, autoimmune diseases, prolactinoma, infertility, impotence, amenorrhea, galactorrhea, acromegaly, Chiari-Frommel syndrome, Argonz-del Castilo syndrome, Forbes-Albright syndrome, and cancer of the breast.

The 19P2L or an amide thereof or a salt therof of the invention is particularly suitable for use as a prophylactic and therapeutic drug in hyperprolactinemia, agalactorrhea, autoimmune diseases, and cancer of the breast.

In addition, the 19P2L or an amide thereof or a salt therof of the invention can be used as a test reagent for study of the prolactin secretory function or a veterinary drug for use as a lactogogue in mammalian farm animals such as bovine, goat, and swine, and is even expected to find application in the elaboration of useful substances in such farm mammals and harvesting of the substances secreted into their milk.

When, in this specification and accompanying drawings, amino acids, peptides, protective groups, active groups, and reagents are represented by abbreviations, the abbreviations adopted by IUPAC-IUB (an international commission on biochemical nomenclature) or those in routine use in the field of the art are employed as can be seen from the following examples. It should also be understood that when any amino acid or the like may occur as optical isomers, the L-form is meant unless otherwise indicated.

DNA: deoxyribonucleic acid
A: adenine
T: thymine
G: guanine
C: cytosine
RNA: ribonucleic acid
EDTA: ethylenediaminetetracetic acid
Gly: glycine
Ala: alanine
Val: valine
Leu: leucine
Ile: isoleucine
Ser: serine
Thr: threonine
Met: methionine
Glu: glutamic acid
Asp: aspartic acid
Lys: lysine
Arg: arginine
His: histidine
Phe: phenylalanine Tyr: tyrosine
Trp: tryptophan
Pro: proline
Asn: asparagine
Gln: glutamine
b19P2L: bovine 19P2L
r19P2L: rat 19P2L
h19P2L: human 19P2L SEQ ID NOs of the SEQUENCE LIST in the specification show the following sequences.

SEQ ID NO:1 shows a nucleotide sequence of the gene coding a fusion protein of the present invention.

SEQ ID NO:2 shows a nucleotide sequence of the gene coding a fusion protein of the present invention.

SEQ ID NO:3 shows a nucleotide sequence of the gene coding a fusion protein of the present invention.

SEQ ID NO:4 shows a nucleotide sequence of the gene coding a fusion protein of the present invention.

SEQ ID NO:5 shows a nucleotide sequence of the gene coding a fusion protein of the present invention.

SEQ ID NO:6 shows a nucleotide sequence of the gene coding a fusion protein of the present invention.

SEQ ID NO:7 shows an amino acid sequence of the bovine 19P2L.

SEQ ID NO:8 shows an amino acid sequence of the rat 19P2L.

SEQ ID NO:9 shows an amino acid sequence of the human 19P2L.

SEQ ID NO:10 shows a nucleotide sequence of the DNA fragment used for synthesizing the DNA obtained in Example 1(a).

SEQ ID NO:11 shows a nucleotide sequence of the DNA fragment used for synthesizing the DNA obtained in Example 1(a).

SEQ ID NO:12 shows a nucleotide sequence of the DNA fragment used for synthesizing the DNA obtained in Example 1(a).

SEQ ID NO:13 shows a nucleotide sequence of the DNA fragment used for synthesizing the DNA obtained in Example 1(a).

SEQ ID NO:14 shows a nucleotide sequence of the DNA fragment used for synthesizing the DNA obtained in Example 1(a).

SEQ ID NO:15 shows a nucleotide sequence of the DNA fragment used for synthesizing the DNA obtained in Example 1(a).

SEQ ID NO:16 shows a nucleotide sequence of the DNA fragment used for constructing pTB960-1-11 and pTB960-12 obtained in Example 1(d).

SEQ ID NO:17 shows a nucleotide sequence of the DNA fragment used for constructing pTB960-1-11 and pTB960-12 obtained in Example 1(d).

SEQ ID NO:18 shows a nucleotide sequence of the DNA fragment used for constructing pTB960-1-11 and pTB960-12 obtained in Example 1(d).

SEQ ID NO:19 shows a nucleotide sequence of the DNA fragment used for constructing pTB960-1-11 and pTB960-12 obtained in Example 1(d).

SEQ ID NO:20 shows a nucleotide sequence of the DNA fragment used for constructing pTB960-1-11 and pTB960-12 obtained in Example 1(d).

SEQ ID NO:21 shows a nucleotide sequence of the DNA fragment used for constructing pTB960-1-11 and pTB960-12 obtained in Example 1(d).

SEQ ID NO:22 shows a nucleotide sequence of the DNA fragment used for constructing pTB960-1-11 and pTB960-12 obtained in Example 1(d).

SEQ ID NO:23 shows a nucleotide sequence of the DNA fragment used for constructing pTB960-1-11 and pTB960-12 obtained in Example 1(d).

SEQ ID NO:24 shows a nucleotide sequence of the DNA fragment used for constructing pTB960-1-11 and pTB960-12 obtained in Example 1(d).

SEQ ID NO:25 shows a nucleotide sequence of the DNA fragment used for constructing pTB960-1-11 and pTB960-12 obtained in Example 1(d).

SEQ ID NO:26 shows a nucleotide sequence of the DNA fragment used for constructing pTB960-1-11 and pTB960-12 obtained in Example 1(d).

SEQ ID NO:27 shows a nucleotide sequence of the DNA fragment used for constructing pTB960-1-11 and pTB960-12 obtained in Example 1(d).

SEQ ID NO:28 shows an amino acid sequence of the substantially equevalent peptide of the peptides comprising the amino acid sequences of SEQ ID NO:7, 8 or 9.

SEQ ID NO:29 shows an amino acid sequence of the bovine pituitary-derived ligand polypeptide which was obtained by purification and analysis of N-terminal sequence for P-3 fraction described in WO97-24436.

SEQ ID NO:30 shows an amino acid sequence of the bovine pituitary-derived ligand polypeptide which was obtained by purification and analysis of N-terminal sequence for P-2 fraction described in WO97-24436.

SEQ ID NO:31 shows an amino acid sequence of the bovine pituitary-derived ligand polypeptide described in WO97-24436.

SEQ ID NO:32 shows an amino acid sequence of the bovine pituitary-derived ligand polypeptide described in WO97-24436.

SEQ ID NO:33 shows an amino acid sequence of the bovine pituitary-derived ligand polypeptide described in WO97-24436.

SEQ ID NO:34 shows an amino acid sequence of the bovine pituitary-derived ligand polypeptide described in WO97-24436.

SEQ ID NO:35 shows an amino acid sequence of the bovine pituitary-derived ligand polypeptide described in WO97-24436.

SEQ ID NO:36 shows an amino acid sequence of the bovine pituitary-derived ligand polypeptide described in WO97-24436.

SEQ ID NO:37 shows an amino acid sequence of the rat pituitary-derived ligand polypeptide described in WO97-24436.

SEQ ID NO:38 shows an amino acid sequence of the rat pituitary-derived ligand polypeptide described in WO97-24436.

SEQ ID NO:39 shows an amino acid sequence of the rat pituitary-derived ligand polypeptide described in WO97-24436.

SEQ ID NO:40 shows an amino acid sequence of the rat pituitary-derived ligand polypeptide described in WO97-24436.

SEQ ID NO:41 shows an amino acid sequence of the rat pituitary-derived ligand polypeptide described in WO97-24436.

SEQ ID NO:42 shows an amino acid sequence of the rat pituitary-derived ligand polypeptide described in WO97-24436.

SEQ ID NO:43 shows an amino acid sequence of the human pituitary-derived ligand polypeptide described in WO97-24436.

SEQ ID NO:44 shows an amino acid sequence of the human pituitary-derived ligand polypeptide described in WO97-24436.

SEQ ID NO:45 shows an amino acid sequence of the human pituitary-derived ligand polypeptide described in WO97-24436.

SEQ ID NO:46 shows an amino acid sequence of the human pituitary-derived ligand polypeptide described in WO97-24436.

SEQ ID NO:47 shows an amino acid sequence of the human pituitary-derived ligand polypeptide described in WO97-24436.

SEQ ID NO:48 shows an amino acid sequence of the human pituitary-derived ligand polypeptide described in WO97-24436.

The transformant *Escherichia coli* MM294 (DE3)/pTB960-10, MM294 (DE3)/pTB960-11, and MM294 (DE3)/pTB960-12 obtained in Example 1 (C) presented hereinafter have all been deposited with Institute for Fermentation, Osaka (IFO) since Jun. 25, 1997 under the accession numbers of IFO 16099, IFO 16100, and IFO 16101, respectively.

The transformant Escherichia coli MM294 (DE3)/pTB960-10, MM294 (DE3)/pTB960-11, and MM294 (DE3)/pTB960-12 obtained in Example 1 (C) presented hereinafter are also on deposit under the terms of the Budapest Treaty from Jun. 15, 1998, with NIBH and has been assigned the Accession Numbers FERMBP-6387, FERMBP-6388 and FERM BP6389 respectively.

The following examples illustrate the present invention in further detail, it being to be understood that the examples are by no means limitative of the scope of the invention.

EXAMPLES

Example 1
Production of a gene coding for b19P2L
(a) Synthesis of DNA fragments

The six DNA fragments (#1 to #6) indicated in FIG. 5 (Sequence Listing: SEQ ID NO:10 to 15) were synthesized from suitably protected DNA β-cyanoethylphosphamidide using Applied Biosystems' Model 380A automated DNA synthesizer. As the protocol for synthesis, the protocol designated by Applied Biosystems was used. The protected DNA oligomer-resin thus synthesized was heated in 2 ml/0.2 μmole resin of concentrated aqueous ammonia at 60° C. for 6 hours. The product was purified by reversed phase high-performance liquid chromatography (hereinafter abbreviated as HPLC) to give a DNA oligomer with the hydroxyl group at 5'-end only had been protected by dimethoxytrityl. This oligomer was treated with 2 ml of 80% acetic acid for 20 minutes to remove the dimethoxytrityl group from the 5'-end and the product was purified by reversed phase HPLC and ion exchange HPLC. The six DNA oligomers synthesized in the above manner are shown in FIG. 5 (SEQ ID NO:10 to 15).

(b) Phosphorylation of DNA oligomers

The four DNA oligomers (#2 to #5) (Sequence Listing: SEQ ID NO:11 to 14) other than #1 (SEQ ID NO:10) for the 5'-end and #6 (SEQ ID NO:15) were respectively reacted in 25 μl of a phosphorylation system [10 μg DNA oligomer, 50 mM Tris-HCl, pH 7.6, 10 mM MgCl$_2$, 1 mM spermidine, 10 mM dithiothreitol (hereinafter abbreviated as DTT), 0.1 mg/ml bovine serum albumin (abbreviated as BSA), 1 mM ATP, 10 U T4 polynucleotide kinase (Takara Shuzo)] at 37° C. for 1 hour to phosphorylate the 5'-ends of the respective oligomers. The reaction mixtures were incubated at 65° C. for 10 minutes, frozen, and thawed for the next reaction.

Figure 6:
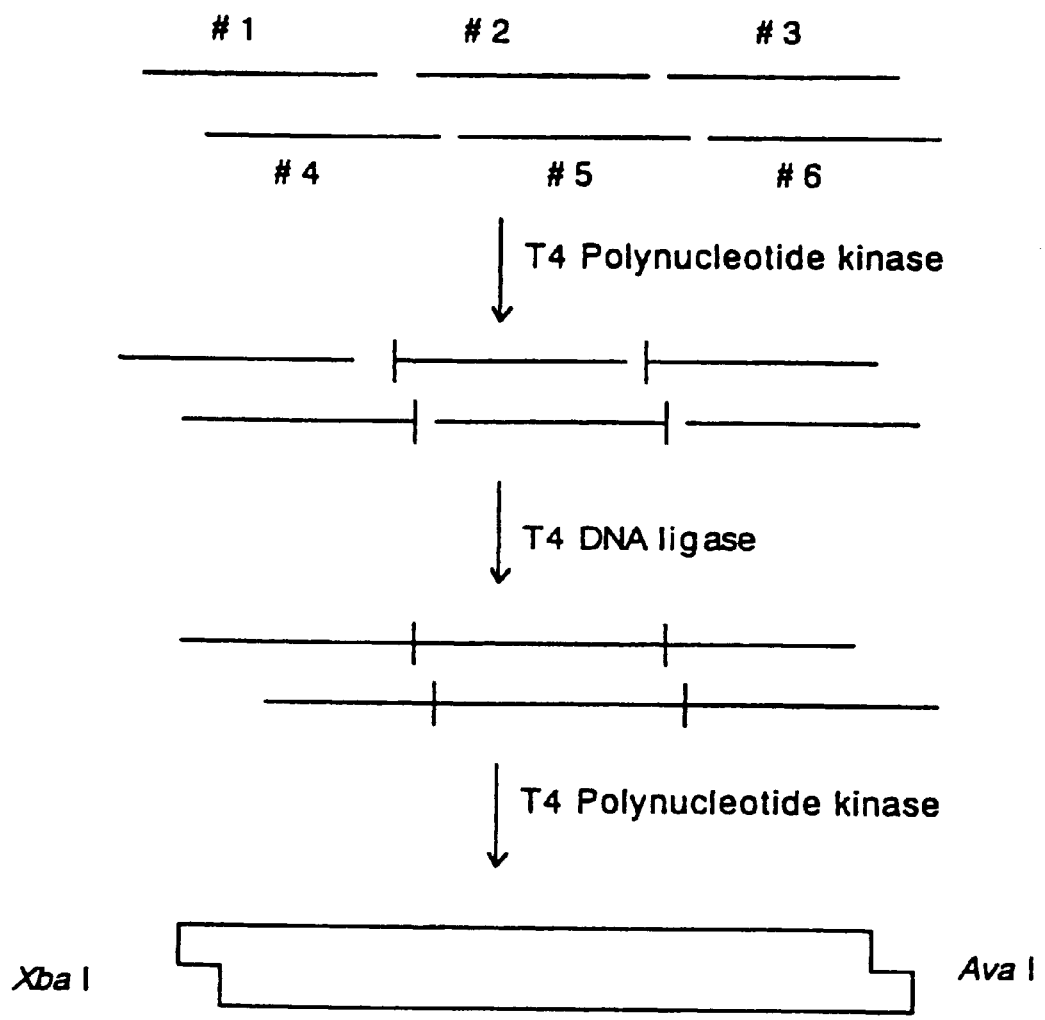
FIG. 6 shows the production figure for bovine 19P2L.

(c) Ligation of DNA fragments (FIG. 6)

The series of steps for constructing the double strand of b19P2L gene is shown in FIG. 6 (where the (•) mark with a projection at the left end indicates that the 5'-end has been phosphorylated). The above 6 DNAs were ligated in the following manner. Thus, 7.5 μl each of the DNA reaction mixtures containing 4 different DNA fragments #2 to #5 (Sequence Listing: SEQ ID NO:11 to 14) respectively as obtained in the above step (b) were combined with 2.5 μg each of #1 and #6 (Sequence Listing: SEQ ID NO:10 and 15) to make a total of 50 μl. Then, 100 μl of buffer (I) and 50 μl of buffer (II) from a DNA Ligation Kit (Takara Shuzo) were added and the mixture was incubated at 16° C. for 16 hours and, then, heated at 65° C. for 10 minutes to stop the reaction. This solution was extracted with two portions of phenol-chloroform, diluted with 2 volumes of ethanol, cooled to −70° C., and centrifuged to recover the DNA as a pellet. In this manner, about 1 μg of a DNA fragment was obtained. This fragment was phosphorylated with T4 polynucleotide kinase (Takara Shuzo) and submitted to the next step (d).

(d) Construction of a b19P2L expression vector (FIG. 7)

As the expression vector, pTB960-2 (EP-A 499990; Koyama et al., Journal of Bacteriology, 32, 273) was used. Thus, 3 μg of pTB960-2 DNA (containing the gene coding for rhbFGF mutein CS23, T7 promoter, and T7 terminator) was digested with AvaI and XbaI (Takara Shuzo) at 37° C. for 4 hours and electrophoresed on a 2% agarose gel to provide a 4.4 kb fragment in the routine manner. This vector fragment and the DNA fragment prepared in (c) above respectively have the single-strand cohesive ends formed on AvaI digestion and XbaI digestion at the corresponding ends. The two fragments were mixed and ligated using buffer (I) from the DNA ligation kit.

Incidentally, this 4.4 kb vector can also be obtained by AvaI and XbaI digestion of the expression vector pTB960-3 or pTB960-7 which can be prepared from the transformant *Escherichia coli* MM294 (DE3)/pTB960-3 (IFO 15241; FERM BP-3615) or *Escherichia coli* MM294 (DE3)/pTB960-7 (IFO 15254; FERM BP-3690), which is described in EP-A-499990, by a per se known procedure.

Using the above reaction mixture, *Escherichia coli* JM109 [Messing, J., Gene, 33, 103–119 (1985)] was transformed in the routine manner. Thus, 50 μl of competent cells [Hanahan, D., J. Mol. Biol., 166, 557 (1983)] stored at −70° C. were cultured at 0° C. for 15 minutes and added to 10 μl of the above reaction mixture. After an additional 30-minute incubation at 0° C., the mixture was further incubated at 42° C. for 1.5 minutes and at 0° C. for an additional 2 minutes. To this reaction mixture was added 200 μl of LB medium (including Bacto tryptone 10 g, Bacto yeast extract 5 g, and NaCl 15 g in each liter), and the mixture was incubated at 37° C for 1 hour. This *E. coli* strain was seeded on LB agar plates containing 12.5 μg/ml of tetracycline, 100 μg/ml of X-Gal, and 0.1 mM IPTG and grown at 37° C. overnight. From among the resulting tetracycline-resistant colonies, 14 β-galactosidase-deficient strains were selected and the transformant plasmid DNAs were crudely purified by the alkali method [Maniatis, T. et al., Molecular Cloning (Cold Spring Harber), 368–369 (1982)] and digested with AvaI and XbaI. A plasmid with a correct restriction pattern was selected and named pTB960-10. For r19P2L and h19P2L, too, the DNA fragments #7 to #12 and #13 to #18 (corresponding to SEQ ID NO:16 to 21 and NO:22 to 27, respectively) were subjected to the same procedures (a to d) as described in Example 1 to construct expression vectors pTB960-11 and pTB960-12. Furthermore, the transformant strains obtained by transforming *Escherichia coli* MM294 (DE3) with those plasmids were designated as MM294 (DE3)/pTB960-10, MM294 (DE3)/pTB960-11, and MM294 (DE3)/pTB960-12, respectively.

(d) Production of b19P2L

MM294 (DE3)/pTB960-10 was grown in 3 ml of LB medium containing 12.5 μg/ml of tetracycline overnight at 37° C. A 1.5 ml portion of the culture was added to 30 ml of the same medium in 200 ml flasks and incubated at 37° C. until a Klett value of about 150 was obtained. Then, isopropyl-1-thio-β-D-galactopyranoside (IPTG) was added at a final concentration of 0.1 mM. After an additional 3-hour incubation, 1 ml of the culture was centrifuged at 15000 rpm (4° C.) for 5 minutes and the cell pellet was dissolved in 100 μl of an aqueous solution containing 0.5 M Tris-HCl (pH 6.8), 10% glycerol, 10% (w/v) sodium dodecyl sulfate (SDS), 0.1% (w/v) R-mercaptoethanol, and bromophenol blue [Laemmli, U.K., Nature, 227, 680(1970)]. The solution was boiled for 3 minutes and subjected to 16% SDS-polyacrylamide electrophoresis (PAGE). Following electrophoresis, the gel was stained with Coomassie Brilliant Blue, whereupon a band was observed in the position corresponding to the molecular mass of b19P2L-hbFGF CS23 mutein partial peptide fusion protein (b19P2L-CS23) (FIG. 8). Referring to FIG. 8, lane 1: molecular weight marker (Bio-Rad, SDS-PAGE Standard Low), lane 2: *E. coli* culture with IPTG (20 μl), and lane 3: *E. coli* culture without IPTG (20 μl).

Example 2

Mass culture of *E. Coli* MM294 (DE3)/pTB960-10

*E. Coli* MM294 (DE3)/pTB960-10 (IFO 16099) was grown on LB plates containing 12.5 μg/ml of tetracycline at 37° C. for 24 hours. A loopful of this culture was inoculated into ml of the same medium in conical flasks of 200 ml capacity and grown under shaking at 37° C. for 24 hours. The resulting culture was transferred to 5 conical flasks of 2 L capacity each containing 1 L of the same medium, 1 ml per flask, and further grown under shaking at 30° C. for 16 hours. The whole amount of the culture was further transferred to a 500 L tank containing 250 L of a medium [identical in composition to the one used in Example 1 (d)] and grown at 30° C. under shaking at 450 rpm. At 5 hours following the beginning of culture, IPTG was added at a final concentration of 420 μM, and the cultivation was completed at the 9th hour. The amount of the cells obtained was 5.3 kg.

Example 3

Using a 50 L tank fermentor, *E. Coli* MM294 (DE3)/pTB960-11 (IFO 16100) was cultured under the same conditions as in Example 2, and 1 kg of cells were harvested from 18 L of the culture broth.

Example 4

Using a 50 L tank fermentor, *E. Coli* MM294 (DE3)/pTB960-12 (IFO 16101) was grown under the same conditions as in Example 2, and 1.1 kg of cells were harvested from 13 L of the culture broth.

Example 5

To 300 g of the cells obtained in Example 2 was added 900 ml of 10 mM EDTA (pH 6.0) and the mixture was sonicated (Branson Sonifier Model 450) and centrifuged (10000 rpm, 60 min.). The supernatant was set aside and the precipitate was subjected to the same procedure again. The pooled supernatant was adjusted to pH 6.0 and applied for adsorption onto an AF-Heparin Toyopearl 650M column (30 mm ID×500 mm L, Tosoh) equilibrated with 50 mM phosphate buffer (pH 6.0). The column was rinsed and a gradient elution was carried out using 0 to 100% B (B=50 mM phosphate buffer+2 M NaCl, pH 6.0) to recover 480 ml of a b19P2L-CS23 fusion protein-containing eluate. This eluate was concentrated using Amicon Diaflow (YM10 membrane, 76 mm φ, Amicon) and further concentrated with constant addition of 0.1 M acetic acid to give a solution of b19P2L-CS23 fusion protein in 0.1 M acetic acid. To this solution was added urea at a final concentration of 6 M, followed by addition of 280 mg of DMAP-CN, and the reaction was carried out at room temperature for 15 minutes. After completion of the reaction, the reaction mixture was applied onto a Sephadex G-25 column (46 mm ID×600 mm L, Pharmacia) equilibrated with 10% acetic acid and an elution was carried out with the same 10% acetic acid as used for column equilibration at a flow rate of 6 ml/min to give an S-cyanated b19P2L-CS23 fusion protein fraction. This eluate was concentrated and desalted using Amicon Diaflow (YM10 membrane, 76 mm φ) to obtain a desalted solution of b19P2L-CS23 fusion protein. To this desalted solution was added urea at a final concentration of 6 M, followed by addition of 25% aqueous ammonia at a final concentration of 3 M, and the reaction was carried out at room temperature for 15 minutes. After completion of the reaction, the reaction mixture was adjusted to pH 6.0 with acetic acid to provide b19P2L (amide form). This reaction mixture was applied onto a Sephadex G-25 column (46 mm ID×600 mm L) equilibrated with 50 mM phosphate buffer (pH 6.0) and an elution was carried out using the same 50 mM phosphate buffer (pH 6.0) as used for column equilibration at a flow rate of 6 ml/min to provide a b19P2L (amide form) fraction. This fraction was applied onto an SP-5PW column (21.5 mm ID×150 mm L, Tosoh) equilibrated with 3 M urea-50 mM phosphate buffer (pH 6.5) for adsorption, and after the column was rinsed, a gradient elution was carried out using 0 to 35% B (B=50 mM phosphate buffer+1 M NaCl+3 M urea, pH 6.5) to recover a b19P2L (amide form) fraction. This fraction was further applied onto a C4P-50 column (21.5 mm ID×300 mm L, Showa Denko) equilibrated with 0.1% trifluoroacetic acid for adsorption and after the column was rinsed, a gradient elution was carried out using 20 to 40% B (B=80% acetonitrile/0.1% trifluoroacetic acid). The resulting b19P2L (amide form) fractions were pooled and lyophilized to provide about 90 mg of freeze-dried powders of b19P2L (amide form).

Example 6

Characterization of b19P2L a) Analysis by SDS-polyacrylamide gel electrophoresis The b19P2L obtained in Example 5 was suspended in sample buffer (Novex Japan) and subjected to electrophoresis on Peptido-Page Mini (TEFCO). After the electrophoresis, the gel was silver-stained (Novex Japan). The sample gave a single band (FIG. 9).

b) Amino acid composition analysis

The amino acid composition was determined with an amino acid analyzer (Hitachi L-8500A Amino Acid Analyzer). The result was in good agreement with the amino acid composition predicted from the cDNA nucleotide sequence of b19P2L (Table 1).

TABLE 1

Amino acid composition analysis

| Amino acid | No. of residues per mole | The value predicted from the nucleotide sequence of b19P2L |
|---|---|---|
| Asx | 2.0 | 2 |
| Thr | 0.9 | 1 |
| Ser | 1.7 | 2 |
| Glx | 2.0 | 2 |
| Pro | 3.2 | 3 |
| Gly | 2.9 | 3 |
| Ala | 3.0 | 3 |
| Cys | — | 0 |
| Val | 1.0 | 1 |
| Met | 1.0 | 1 |
| Ile | 3.0 | 3 |
| Leu | 0 | 0 |
| Tyr | 1.0 | 1 |
| Phe | 1.0 | 1 |
| His | 1.9 | 2 |
| Lys | 0 | 0 |
| Arg | 4.8 | 5 |
| Trp | 0.9 | 1 |

Acid hydrolysis (6N hydrochloric acid-4% thioglycolic acid, 110° C., 24 hr)
— Not detected c) Determination of the N-terminal amino acid sequence The N-terminal amino acid sequence was determined with a gas-phase protein sequencer (Applied Biosystems Model 477A). The result was in good agreement with the N-terminal amino acid sequence predicted from the cDNA nucleotide sequence of b19P2L [Table 2].

TABLE 2

N-terminal amino acid sequence

| Residue No. | PTH[1]-amino acid detected (pmol) | Amino acid predicted from the nucleotide sequence of b19P2L |
|---|---|---|
| 1 | Ser(188) | Ser |
| 2 | Arg(54) | Arg |
| 3 | Ala(650) | Ala |
| 4 | His(128) | His |
| 5 | Gln(430) | Gln |
| 6 | His(95) | His |
| 7 | Ser(80) | Ser |
| 8 | Met(216) | Met |
| 9 | Glu(193) | Glu |
| 10 | Ile(245) | Ile |
| 11 | Arg(90) | Arg |
| 12 | Thr(143) | Thr |
| 13 | Pro(148) | Pro |
| 14 | Asp(65) | Asp |
| 15 | Ile(245) | Ile |
| 16 | Asn(128) | Asn |
| 17 | Pro(142) | Pro |
| 18 | Ala(129) | Ala |
| 19 | Trp(46) | Trp |
| 20 | Tyr(32) | Tyr |

Analyzed for 1 nmol
[1] Phenylthiohydantoin d) C-terminal amino acid analysis

The C-terminal amino acid was analyzed with an amino acid analyzer (Hitachi L-8500A Amino Acid Analyzer). However, because the C-terminus had been amidated, no detection could be made (Table 3).

TABLE 3

C-terminal amino acid analysis

| b19P2L | C-terminal amino acid | Recovery (%) |
|---|---|---|
| | Phe | — |

Gas-phase hydrazinolysis (100° C., 6 hr)

Example 7
Determination of biological activity

In accordance with the method described in Japanese Patent Application H8-348328(WO97-24436), the arachidonic acid metabolite-releasing activity of the b19P2L obtained in Example 5 was assayed. The activity was equivalent to the activity of the synthetic b19P2L(amido form).

Example 8

Using 100 g of the cells obtained in Example 3, the procedure of Example 5 was otherwise repeated to provide about 4 mg of r19P2L(amido form).

Example 9

Using 300 g of the cells obtained in Example 4, the procedure of Example 5 was otherwise repeated to provide about 13 mg of h19P2L(amido form).

Example 10
Characterization of the r19P2L(amido form) obtained in Example 8
a) Amino acid composition analysis The amino acid sequence of the r19P2L(amido form) obtained in Example 8 was determined with an amino acid analyzer (Hitachi L-8500A Amino Acid Analyzer). The result was in good agreement with the amino acid composition predicted from the cDNA nucleotide sequence of r19P2L [Table 4].

TABLE 4

Amino acid composition analysis

| Amino acid | No. of residues per mole | The value predicted from the nucleotide sequence of r19P2L |
|---|---|---|
| Asx | 1.9 | 2 |
| Thr[1] | 2.8 | 3 |
| Ser[1] | 1.9 | 2 |
| Glx | 1.9 | 2 |
| Pro | 3.1 | 3 |
| Gly | 3.0 | 3 |
| Ala | 2.0 | 2 |
| Cys[2] | | 0 |
| Val | 1.0 | 1 |
| Met | 1.0 | 1 |
| Ile | 2.0 | 2 |
| Leu | 0 | 0 |
| Tyr | 1.0 | 1 |
| Phe | 1.0 | 1 |
| His | 2.1 | 2 |
| Lys | 0 | 0 |
| Arg | 5.1 | 5 |
| Trp[2] | | 1 |

Acid hydrolysis (6N HCl, 110° C., average of 24-hr and 48-hr hydrolyses)
[1] The value extrapolated to 0 hr.
[2] Not detected b) Determination of N-terminal amino acid sequence The N-terminal amino acid sequence of the r19P2L (amido form) obtained in Example 8 was determined using a gas-phase protein sequencer (Applied Biosystems Model 477A). The result was in complete agreement with the N-terminal amino acid sequence predicted from the cDNA nucleotide sequence of r19P2L(amido form) [Table 5].

TABLE 5

N-terminal amino acid sequence

| Residue No. | PTH[1])-amino acid detected (pmol) | Amino acid predicted from the nucleotide sequence of r19P2L |
|---|---|---|
| 1 | Ser(340) | Ser |
| 2 | Arg(105) | Arg |
| 3 | Ala(1343) | Ala |
| 4 | His(457) | His |
| 5 | Gln(1177) | Gln |
| 6 | His(411) | His |
| 7 | Ser(448) | Ser |
| 8 | Met(1050) | Met |
| 9 | Glu(590) | Glu |
| 10 | Thr(493) | Thr |
| 11 | Arg(357) | Arg |
| 12 | Thr(405) | Thr |
| 13 | Pro(569) | Pro |
| 14 | Asp(371) | Asp |
| 15 | Ile(467) | Ile |
| 16 | Asn(417) | Asn |
| 17 | Pro(438) | Pro |
| 18 | Ala(365) | Ala |
| 19 | Trp(160) | Trp |
| 20 | Tyr(302) | Tyr |

Analyzed for 1.5 nmol
[1])Phenylthiohydantoin c) C-terminal amino acid analysis

The C-terminal amino acid of the r19P2L(amido form) obtained in Example 8 was analyzed with an amino acid sequencer (Hitachi L-8500A Amino Acid Analyzer). However, because the C-terminus had been amidated, no detection could be made (Table 6).

TABLE 6

C-terminal amino acid analysis

| r19P2L | C-terminal amino acid | Recovery (%) |
|---|---|---|
|  | Phe | — |

Gas-phase hydrazinolysis (100° C., 6 hr)

Example 11
Determination of biological activity

In accordance with the procedures described in Japanese Patent Application H8-348328 (WO97-24436), arachidonic acid metabolite-releasing activity and receptor binding assays were carried out using the r19P2L(amido form) obtained in Example 8. As a result, the sample was found to be as active as the synthetic r19P2L(amido form).

Example 12
Characterization of the h19P2L(amido form) obtained in Example 9
a) Amino acid analysis The amino acid sequence of the h19P2L(amido form) obtained in Example 9 was determined with an amino acid analyzer (Hitachi L-8500A Amino Acid Analyzer). The result was in good agreement with the amino acid composition predicted from the cDNA nucleotide sequence of h19P2L(amido form) [Table 7].

TABLE 7

Amino acid composition analysis

| Amino acid | No. of residues per mole | The value predicted from the nucleotide sequence of h19P2L |
|---|---|---|
| Asx | 2.0 | 2 |
| Thr[1]) | 2.0 | 2 |
| Ser[1]) | 3.1 | 3 |
| Glx | 1.0 | 1 |
| Pro | 3.0 | 3 |
| Gly | 2.1 | 2 |
| Ala | 2.0 | 2 |
| Cys[2]) |  | 0 |
| Val | 1.0 | 1 |
| Met | 1.0 | 1 |
| Ile | 2.9 | 3 |
| Leu | 0 | 0 |
| Tyr | 1.0 | 1 |
| Phe | 0.9 | 1 |
| His | 2.0 | 2 |
| Lys | 0 | 0 |
| Arg | 5.9 | 6 |
| Trp[2]) |  | 1 |

Acid hydrolysis (6N HCl, 110° C., average of 24-hr and 48-hr hydrolyses)
[1])The value extrapolated to 0 hr.
[2])Not detected b) Determination of N-terminal amino acid sequence The N-terminal amino acid sequence of the h19P2L (amido form) obtained in Example 9 was determined using a gas-phase protein sequencer (Applied Biosystems Model 477A). The result was in complete agreement with the N-terminal amino acid sequence predicted from the cDNA nucleotide sequence of h19P2L(amido form) [Table 8].

TABLE 8

N-terminal amino acid sequence

| Residue No. | PTH[1])-amino acid detected (pmol) | Amino acid predicted from the nucleotide sequence of h19P2L |
|---|---|---|
| 1 | Ser(1172) | Ser |
| 2 | Arg(359) | Arg |
| 3 | Thr(1173) | Thr |
| 4 | His(599) | His |
| 5 | Arg(1045) | Arg |
| 6 | His(897) | His |
| 7 | Ser(1169) | Ser |
| 8 | Met(2946) | Met |
| 9 | Glu(1249) | Glu |
| 10 | Ile(1828) | Ile |
| 11 | Arg(1202) | Arg |
| 12 | Thr(1289) | Thr |
| 13 | Pro(1210) | Pro |
| 14 | Asp(856) | Asp |
| 15 | Ile(1114) | Ile |
| 16 | Asn(862) | Asn |
| 17 | Pro(862) | Pro |
| 18 | Ala(1308) | Ala |
| 19 | Trp(290) | Trp |
| 20 | Tyr(466) | Tyr |

Analyzed for 3.0 nmol
[1])Phenylthiohydantoin c) C-terminal amino acid analysis

The C-terminal amino acid of the h19P2L(amido form) obtained in Example 9 was analyzed with an amino acid sequencer (Hitachi L-8500A Amino Acid Analyzer). However, because the C-terminus had been amidated, no detection could be made (Table 9).

TABLE 9

C-terminal amino acid analysis

| r19P2L | C-terminal amino acid | Recovery (%) |
|---|---|---|
| | Phe | — |

Gas-phase hydrazinolysis (100° C., 6 hr)

Example 13
Determination of biological activity

In accordance with the procedures described in Japanese Patent Application H8-348328 (WO97-24436), arachidonic acid metabolite-releasing activity and receptor binding assays were carried out using the h19P2L(amido form) obtained in Example 9. As a result, the sample was found to be as active as the synthetic h19P2L(amido form).

Example 14

To 250 g of the cells obtained in Example 3 was added 900 ml of 10 mM EDTA (pH 6.0), and the mixture was sonicated (Branson Sonifier Model 450) and centrifuged (10000 rpm, 60 min.). Using the pellet obtained, the above procedure was repeated twice. The final pellet was dissolved in 500 ml of 6 M guanidine HCl-0.2 M Tris/HCl buffer (pH 8.0). This solution was added to 10 L of 50 mM Tris/HCl buffer (pH 8.0) containing 1 mM DTT and 0.6 M arginine and the mixture was incubated at 4° C. overnight for activation. The activated mixture was adjusted to pH 6.0 with concentrated hydrochloric acid and applied onto an AF-Heparin Toyopearl 650 M column (30 mm ID×500 mm L, Tosoh) equilibrated with 50 mM phosphate buffer (pH 6.0) for adsorption. The column was rinsed and a gradient elution was carried out using 0 to 100% B (B=50 mM phosphate buffer+2 M NaCl, pH 6.0) to recover 500 ml of a r19P2L-CS23 fusion protein-containing eluate. This eluate was concentrated using Amicon Diaflow (YM10 membrane, 76 mm φ, Amicon) and further concentrated with constant addition of 0.1 Macetic acid to recover a solution of r19P2L-CS23fusion protein in 0.1 M acetic acid. To this solution was added urea at a final concentration of 6 M, followed by addition of 106 mg of DMAP-CN, and the reaction was carried out at room temperature for 15 minutes. After completion of the reaction, the reaction mixture was applied onto a Sephadex G-25 column (46 mm ID×600 mm L, Pharmacia) equilibrated with 10% acetic acid and an elution was carried out with the same 10% acetic acid as used for column equilibration at a flow rate of 6 ml/min to obtain an S-cyanated r19P2L-CS23 fusion protein fraction. This eluate was concentrated and desalted through Amicon Diaflow (YM10 membrane, 76 mm φ) to provide a desalted solution of r19P2L-CS23 fusion protein. To this desalted solution was added urea at a final concentration of 6 M, followed by addition of 25% aqueous ammonia at a final concentration of 3 M, and the reaction was conducted at room temperature for 15 minutes. After completion of the reaction, the reaction mixture was adjusted to pH 6.0 with acetic acid to provide r19P2L. This reaction mixture was applied onto a Sephadex G-25 column (46 mm ID×600 mm L) equilibrated with 50 mM phosphate buffer (pH 6.0) and an elution was carried out with the same 50 mM phosphate buffer (pH 6.0) as used for column equilibration at a flow rate of 6 ml/min to provide a r19P2L fraction. This r19P2L fraction was applied onto an SP-5PW column (21.5 mm ID×150 mm L, Tosoh) equilibrated with 3 M urea-50 mM phosphate buffer (pH 6.5) for adsorption. After the column was rinsed, a gradient elution was carried out with 0 to 35% B (B=50 mM phosphate buffer+1 M NaCl+3 M urea, pH 6.5) to obtain an r19P2L-containing eluate. This r19P2L-containing eluate was further applied onto a C4P-50 column (21.5 mm ID×300 mm L, Showa Denko) equilibrated with 0.1% trifluoroacetic acid for adsorption and after the column was rinsed, a gradient elution was carried out with 20 to 40% B (B: 80% acetonitrile/0.1% trifluoroacetic acid). The r19P2L fractions were pooled and lyophilized to provide about 27 mg of freezed-dried r19P2L powders.

Example 15
Characterization of the r19P2L obtained in Example 14
a) Amino acid analysis The amino acid sequence of the r19P2L(amido form) obtained in Example 14 was determined with an amino acid analyzer (Hitachi L-8500A Amino Acid Analyzer). The result was in good agreement with the amino acid composition predicted from the cDNA nucleotide sequence of r19P2L(amido form) [Table 10].

TABLE 10

Amino acid analysis

| Amino acid | No. of residues per mole | The value predicted from the nucleotide sequence of r19P2L |
|---|---|---|
| Asx | 1.9 | 2 |
| Thr[1] | 2.6 | 3 |
| Ser[1] | 1.5 | 2 |
| Glx | 2.0 | 2 |
| Pro | 3.2 | 3 |
| Gly | 3.0 | 3 |
| Ala | 2.2 | 2 |
| Cys[2] | | 0 |
| Val | 1.1 | 1 |
| Met | 0.9 | 1 |
| Ile | 2.0 | 2 |
| Leu | 0 | 0 |
| Tyr | 1.0 | 1 |
| Phe | 1.0 | 1 |
| His | 2.2 | 2 |
| Lys | 0 | 0 |
| Arg | 5.3 | 5 |
| Trp | 0.8 | 1 |

Acid hydrolysis (6N HCl-4% thioglycolic acid, 110° C., average of 24-hr and 48-hr hydrolyses)
[1]The value extrapolated to 0 hr.
[2]Not detected b) Determination of N-terminal amino acid sequence The N-terminal amino acid sequence of the r19P2L (amido form) obtained in Example 14 was determined using a gas-phase protein sequencer (Applied Biosystems Model 477A). The result was in complete agreement with the N-terminal amino acid sequence predicted from the cDNA nucleotide sequence of r19P2L(amido form) [Table 11].

TABLE 11

N-terminal amino acid sequence

| Residue No. | PTH[1]-amino acid detected (pmol) | Amino acid predicted from the nucleotide sequence of r19P2L |
|---|---|---|
| 1 | Ser(150) | Ser |
| 2 | Arg(395) | Arg |
| 3 | Ala(507) | Ala |
| 4 | His(352) | His |
| 5 | Gln(327) | Gln |

TABLE 11-continued

N-terminal amino acid sequence

| Residue No. | PTH[1])-amino acid detected (pmol) | Amino acid predicted from the nucleotide sequence of r19P2L |
|---|---|---|
| 6 | His(241) | His |
| 7 | Ser(99) | Ser |
| 8 | Met(288) | Met |
| 9 | Glu(171) | Glu |
| 10 | Thr(93) | Thr |
| 11 | Arg(72) | Arg |
| 12 | Thr(45) | Thr |
| 13 | Pro(109) | Pro |
| 14 | Asp(57) | Asp |
| 15 | Ile(51) | Ile |
| 16 | Asn(38) | Asn |
| 17 | Pro(41) | Pro |
| 18 | Ala(23) | Ala |
| 19 | Trp(26) | Trp |
| 20 | Tyr(10) | Tyr |

Analyzed for 1 nmol
[1])Phenylthiohydantoin d) C-terminal amino acid analysis

The C-terminal amino acid of the r19P2L(amido form) obtained in Example 14 was analyzed with an amino acid sequencer (Hitachi L-8500A Amino Acid Analyzer). However, because the C-terminus had been amidated, no detection could be made (Table 12).

TABLE 12

C-terminal amino acid analysis

| r19P2L | C-terminal amino acid | Recovery (%) |
|---|---|---|
|  | Phe | — |

Gas-phase hydrazinolysis (100° C., 6 hr)

Example 16
Determination of biological activity

In accordance with the procedures described in Japanese Patent Application H8-348328 (WO97-24436), arachidonic acid metabolite-releasing activity and receptor binding assays were carried out with the r19P2L(amido form) obtained in Example 14. As a result, the sample was found to be as active as the synthetic r19P2L(amido form).

Example 17

To 250 g of the cells obtained in Example 3 was added 900 ml of 10 mM EDTA (pH 6.0), and the mixture was sonicated (Branson Sonifier Model 450) and centrifuged (10000 rpm, 60 min.). The supernatant was set aside and the pellet was subjected to the same procedure again. The pooled supernatant was adjusted to pH 6.0 and applied for adsorption onto an AF-Heparin Toyopearl 650M column (30 mm ID×500 mm L, Tosoh) equilibrated with 50 mM phosphate buffer (pH 6.0). The column was rinsed and a gradient elution was carried out using 0 to 100% B (B=50 mM phosphate buffer+2 M NaCl, pH 6.0) to recover 500 ml of an r19P2L-CS23 fusion protein-containing eluate. This eluate was concentrated using Amicon Diaflow (YM10 membrane, 76 mm φ, Amicon) and further concentrated with constant addition of 0.1 M acetic acid to give 300 ml of a solution of r19P2L-CS23 fusion protein in 0.1 M acetic acid. A 15 ml portion of this solution was dialyzed against 6 M urea-containing 0.1 M phosphate buffer (pH 6.0). After—completion of dialysis, 250 μl of 0.1 M 2,2'-dithiopyridine-methanol solution was added and the reaction was carried out at room temperature for 1 hour. After completion of the reaction, the reaction mixture was dialyzed against 6 M urea-containing 0.1 M phosphate buffer (pH 5.0). Thereafter, 6.6 mg of potassium cyanide was added and the reaction was carried out at room temperature for 1 hour. After completion of the reaction, the reaction mixture was dialyzed against 6 M urea. Thereafter, 25% aqueous ammonia was added at a final concentration of 3 M, and the reaction was carried out at room temperature for 15 minutes. After completion of the reaction, the reaction mixture was adjusted to pH 6.0 with acetic acid. This reaction mixture was applied onto a Sephadex G-25 column (46 mm ID×600 mm L) equilibrated with 50 mM phosphate buffer (pH 6.0) and an elution was carried out using the same 50 mM phosphate buffer (pH 6.0) as used for column equilibration at a flow rate of 6 ml/min to provide an r19P2L-containing eluate. This r19P2L-containing eluate was applied onto an SP-5PW column (21.5mm ID×150mm L, Tosoh) equilibrated with 3 M urea-50 mM phosphate buffer (pH 6.5) and after the column was rinsed, a gradient elution was carried out using 0 to 35% B (B=50 mM phosphate buffer+1 M NaCl+3 M urea, pH 6.5) to recover an r19P2L-containing eluate. This r19P2L-containing eluate was further applied onto a C4P-50 column (21.5 mm ID×300 mm L, Showa Denko) equilibrated with 0.1% trifluoroacetic acid and after the column was rinsed, a gradient elution was carried out using 20 to 40% B (B=80% acetonitrile/0.1% trifluoroacetic acid). The resulting r19P2L fractions were pooled and lyophilized to provide about 4 mg of freeze-dried powders of r19P2L.

Example 18

Characterization of the r19P2L(amido form) obtained in Example 17 a) Amino acid analysis

The amino acid sequence was determined with an amino acid analyzer (Hitachi L-8500A Amino Acid Analyzer). The result was in good agreement with the amino acid composition predicted from the cDNA nucleotide sequence of r19P2L(amido form) [Table 13].

TABLE 13

Amino acid analysis

| Amino acid | No. of residues per mole | The value predicted from the nucleotide sequence of r19P2L |
|---|---|---|
| Asx | 1.9 | 2 |
| Thr[1]) | 2.8 | 3 |
| Ser[1]) | 1.6 | 2 |
| Glx | 2.0 | 2 |
| Pro | 3.3 | 3 |
| Gly | 3.1 | 3 |
| Ala | 2.2 | 2 |
| Cys[2]) |  | 0 |
| Val | 1.1 | 1 |
| Met | 1.0 | 1 |
| Ile | 2.0 | 2 |
| Leu | 0 | 0 |
| Tyr | 1.0 | 1 |

TABLE 13-continued

Amino acid analysis

| Amino acid | No. of residues per mole | The value predicted from the nucleotide sequence of r19P2L |
|---|---|---|
| Phe | 1.1 | 1 |
| His | 2.2 | 2 |
| Lys | 0 | 0 |
| Arg | 5.3 | 5 |
| Trp[2)] | 0.8 | 1 |

Acid hydrolysis (6N HCl-4% thioglycolic acid, 110° C., average of 24-hr and 48-hr hydrolyses)
[1)]The value extrapolated to 0 hr.
[2)]Not detected b) Determination of the N-terminal amino acid sequence The N-terminal amino acid sequence of the r19P2L (amido form) obtained in Example 17 was determined using a gas-phase protein sequencer (Applied Biosystems Model 477A). The result was in complete agreement with the N-terminal amino acid sequence predicted from the cDNA nucleotide sequence of r19P2L(amido form) [Table 14].

TABLE 14

N-terminal amino acid sequence

| Residue No. | PTH[1)]-amino acid detected (pmol) | Amino acid predicted from the nucleotide sequence of r19P2L |
|---|---|---|
| 1 | Ser (332) | Ser |
| 2 | Arg (438) | Arg |
| 3 | Ala (766) | Ala |
| 4 | His (113) | His |
| 5 | Gln (420) | Gln |
| 6 | His (255) | His |
| 7 | Ser (163) | Ser |
| 8 | Met (405) | Met |
| 9 | Glu (192) | Glu |
| 10 | Thr (169) | Thr |
| 11 | Arg (233) | Arg |
| 12 | Thr (113) | Thr |
| 13 | Pro (145) | Pro |
| 14 | Asp (97) | Asp |
| 15 | Ile (91) | Ile |
| 16 | Asn (97) | Asn |
| 17 | Pro (92) | Pro |
| 18 | Ala (57) | Ala |
| 19 | Trp (35) | Trp |
| 20 | Tyr (42) | Tyr |

Analyzed for 1 nmol
[1)]Phenylthiohydantoin d) C-terminal amino acid analysis

The C-terminal amino acid of the r19P2L(amido form) obtained in Example 17 was analyzed with an amino acid sequencer (Hitachi L-8500A Amino Acid Analyzer). However, because the C-terminus had been amidated, no detection could be made (Table 15).

TABLE 15

C-terminal amino acid analysis r19P2L

| C-terminal amino acid | Recovery (%) |
|---|---|
| Phe | — |

Gas-phase hydrazinolysis (100° C., 6 hr)

Example 19
Determination of biological activity

In accordance with the procedures described in Japanese Patent Application H8-348328 (WO97-24436), arachidonic acid metabolite-releasing activity and receptor binding assays were carried out with the r19P2L(amido form) obtained in Example 17. As a result, the sample was found to be as active as the synthetic r19P2L(amido form).

Example 20

Using 300 g of the cells obtained in Example 4, the procedure of Example 17 was otherwise repeated to provide about 70 mg of freeze-dried powders of h19P2L(amido form).

b) Amino acid analysis

The amino acid sequence was determined with an amino acid analyzer (Hitachi L-8500A Amino Acid Analyzer). The result was in good agreement with the amino acid composition predicted from the cDNA nucleotide sequence of h19P2L(amido form) [Table 16].

TABLE 16

Amino acid composition analysis

| Amino acid | No. of residues per mole | The value predicted from the nucleotide sequence of h19P2L |
|---|---|---|
| Asx | 1.9 | 2 |
| Thr[1)] | 2.0 | 2 |
| Ser[1)] | 2.5 | 3 |
| Glx | 1.0 | 1 |
| Pro | 3.0 | 3 |
| Gly | 1.9 | 2 |
| Ala | 1.9 | 2 |
| Cys[2)] | | 0 |
| Val | 1.0 | 1 |
| Met | 1.0 | 1 |
| Ile | 3.0 | 3 |
| Leu | 0 | 0 |
| Tyr | 1.0 | 1 |
| Phe | 1.0 | 1 |
| His | 2.1 | 2 |
| Lys | 0 | 0 |
| Arg | 6.0 | 6 |
| Trp[2)] | 1.1 | 1 |

Acid hydrolysis (6N HCl-4% thioglycolic acid, 110° C., average of 24-hr and 48-hr hydrolyses)
[1)]The value extrapolated to 0 hr.
[2)]Not detected b) Determination of the N-terminal amino acid sequence The N-terminal amino acid sequence was determined with a gas-phase protein sequencer (Applied Biosystems Model 477A). The result was in complete agreement with the N-terminal amino acid sequence predicted from the cDNA nucleotide sequence of h19P2L(amido form) [Table 17].

TABLE 17

N-terminal amino acid sequence

| Residue No. | PTH[1])-amino acid detected (pmol) | Amino acid predicted from the nucleotide sequence of h19P2L |
|---|---|---|
| 1 | Ser (578) | Ser |
| 2 | Arg (140) | Arg |
| 3 | Thr (542) | Thr |
| 4 | His (306) | His |
| 5 | Arg (630) | Arg |
| 6 | His (365) | His |
| 7 | Ser (166) | Ser |
| 8 | Met (436) | Met |
| 9 | Ile (298) | Ile |
| 10 | Thr (298) | Thr |
| 11 | Arg (254) | Arg |
| 12 | Thr (117) | Thr |
| 13 | Pro (200) | Pro |
| 14 | Asp (141) | Asp |
| 15 | Ile (188) | Ile |
| 16 | Asn (94) | Asn |
| 17 | Pro (145) | Pro |
| 18 | Ala (152) | Ala |
| 19 | Trp (63) | Trp |
| 20 | Tyr (91) | Tyr |

Analyzed for 1 nmol
[1])Phenylthiohydantoin d) C-terminal amino acid analysis

The C-terminal amino acid was analyzed with an amino acid sequencer (Hitachi L-8500A Amino Acid Analyzer). However, because the C-terminus had been amidated, no detection could be made (Table 18).

TABLE 18

C-terminal amino acid analysis h19P2L

| C-terminal amino acid | Recovery (%) |
|---|---|
| Phe | — |

Gas-phase hydrazinolysis (100° C., 6 hr)

Example 21
Determination of biological activity

In accordance with the procedures described in Japanese Patent Application H8-348328 (WO97-24436), arachidonic acid metabolite-releasing activity and receptor binding assays were carried out with the h19P2L obtained in Example 20. As a result, the sample was found to be as active as the synthetic h19P2L(amido form).

[Effects of the Invention]

The method of the present invention is suitable for the commercial high-level production of a protein or peptide (19P2L) which can be used as a prophylactic and therapeutic drug for various diseases such as senile dementia, cerebrovascular dementia (dementia arising from cerebrovascular disorders), dementia associated with genealogical retroplastic diseases (e.g. Alzheimer's disease, Parkinson's disease, Pick's disease, Huntington's disease, etc.), dementia associated with infectious diseases (e.g. Creutzfeldt-Jakob's and other slow virus diseases), dementia associated with endocrine or metabolic disease or toxicosis (e.g. hypothyroidism, vitamin B12 deficiency, alcoholism, intoxication by drugs, metals, and organic compounds), dementia associated with tumorigenic diseases (e.g. brain tumor), dementia associated with traumatic diseases (e.g. chronic subarachnoidal hemorrhage), and other types of dementia, depression, hyperactive child syndrome (microencephalopathy), and disturbance of consciousness.

The ligand polypeptide of the present invention has prolactin secretion-stimulating and -inhibiting activities. Thus, the ligand polypeptide of the invention has prolactin secretion-stimulating activity and, therefore, finds application as a prophylactic and therapeutic drug for various diseases associated with prolactin hyposecretion. On the other hand, the ligand polypeptide of the invention has a high affinity for the receptor proteins and, therefore, when used in an increased dose, causes desensitization for prolactin secretion, thus exhibiting prolactin secretion-inhibiting activity. In this sense, it can be used as a prophylactic and therapeutic drug for various diseases associated with prolactin hypersecretion.

Futhermore, the 19P2L or an amide thereof or a salt therof of the invention can be used with advantage as a prolactin secretion-stimulating agent for the prevention and treatment of certain diseases associated with prolactin secretion, such as hypoovarianism, seminal vesicle hypoplasia, osteoporosis, menopausal syndrome, agalactorrhea, hypothyroidism, and renal failure.

On the other hand, the 19P2L or an amide thereof or a salt therof of the invention can be used with advantage as a prolactin secretion-inhibitory agent in the prevention and treatment of certain diseases associated with prolactin secretion, such as hyperprolactinemia, pituitary adenoma, tumor of diencephalon, emmeniopathy, stress, autoimmune diseases, prolactinoma, infertility, impotence, amenorrhea, galactorrhea, acromegaly, Chiari-Frommel syndrome, Argonz-del Castilo syndrome, Forbes-Albright syndrome, and cancer of the breast.

What is claimed is:

1. A method of producing a 19P2 ligand or an amide thereof or a salt thereof, wherein the 19P2 ligand is bovine 19P2 ligand (SEQ ID NO: 7), rat 19P2 ligand (SEQ ID NO: 8), or human 19P2 ligand (SEQ ID NO:9) and wherein the method comprises subjecting the fusion protein or peptide comprising the 19P2 ligand fused to a protein or a peptide having a cysteine residue at the N-terminus to a reaction for cleavage of the peptide bond on the amino terminal side of the cysteine residue.

2. The method of claim 1 wherein the reaction for cleavage of the peptide bond on the amino-terminal side of the cysteine residue comprises 1) cyanylation followed by 2) ammonolysis or hydrolysis.

3. The method of claim 1 wherein the reaction for cleavage of the peptide bond on the amino-terminal side of the cysteine residue comprises 1) cyanylation followed by 2) ammonolysis to produce the amide of 19P2 ligand or a salt thereof.

* * * * *

SEQUENCE LISTING (1) GENERAL INFORMATION:

(iii) NUMBER OF SEQUENCES: 52

(2) INFORMATION FOR SEQ ID NO:1:

(i) SEQUENCE CHARACTERISTICS:
      (A) LENGTH: 528 base pairs
      (B) TYPE: nucleic acid
      (C) STRANDEDNESS: double
      (D) TOPOLOGY: linear (ii) MOLECULE TYPE: synthetic DNA (xi) SEQUENCE DESCRIPTION: SEQ ID NO:1:

| | | | | | |
|---|---|---|---|---|---|
| TCCCGTGCTC | ACCAGCACTC | CATGGAAATC | CGTACCCCGG | ACATCAACCC | GGCTTGGTAC | 60
| GCTGGTCGTG | GTATCCGTCC | GGTTGGTCGT | TTCTGCCCCG | AGGATGGCGG | CAGCGGCGCC | 120
| TTCCCGCCCG | GCCACTTCAA | GGACCCCAAG | CGGCTGTACT | GCAAAAACGG | GGGCTTCTTC | 180
| CTGCGCATCC | ACCCCGACGG | CCGAGTTGAC | GGGGTCCGGG | AGAAGAGCGA | CCCTCACATC | 240
| AAGCTACAAC | TTCAAGCAGA | AGAGAGAGGA | GTTGTGTCTA | TCAAAGGAGT | GAGCGCTAAT | 300
| CGTTACCTGG | CTATGAAGGA | AGATGGAAGA | TTACTAGCTT | CTAAGTCTGT | TACGGATGAG | 360
| TGTTTCTTTT | TTGAACGATT | GGAATCTAAT | AACTACAATA | CTTACCGGTC | AAGGAAATAC | 420
| ACCAGTTGGT | ATGTGGCACT | GAAACGAACT | GGGCAGTATA | AACTTGGATC | CAAAACAGGA | 480
| CCTGGGCAGA | AAGCTATACT | TTTTCTTCCA | ATGTCTGCTA | AGAGCTGC | | 528

(2) INFORMATION FOR SEQ ID NO:2:

(i) SEQUENCE CHARACTERISTICS:
        (A) LENGTH: 528 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:2:

| | | | | | |
|---|---|---|---|---|---|
| TCCCGTGCTC | ACCAGCACTC | CATGGAAATC | CGTACCCCGG | ACATCAACCC | GGCTTGGTAC | 60
| GCTGGTCGTG | GTATCCGTCC | GGTTGGTCGT | TTCTGTCCCG | AGGATGGCGG | CAGCGGCGCC | 120
| TTCCCGCCCG | GCCACTTCAA | GGACCCCAAG | CGGCTGTACT | GCAAAAACGG | GGGCTTCTTC | 180
| CTGCGCATCC | ACCCCGACGG | CCGAGTTGAC | GGGGTCCGGG | AGAAGAGCGA | CCCTCACATC | 240
| AAGCTACAAC | TTCAAGCAGA | AGAGAGAGGA | GTTGTGTCTA | TCAAAGGAGT | GAGCGCTAAT | 300
| CGTTACCTGG | CTATGAAGGA | AGATGGAAGA | TTACTAGCTT | CTAAGTCTGT | TACGGATGAG | 360
| TGTTTCTTTT | TTGAACGATT | GGAATCTAAT | AACTACAATA | CTTACCGGTC | AAGGAAATAC | 420
| ACCAGTTGGT | ATGTGGCACT | GAAACGAACT | GGGCAGTATA | AACTTGGATC | CAAAACAGGA | 480
| CCTGGGCAGA | AAGCTATACT | TTTTCTTCCA | ATGTCTGCTA | AGAGCTGC | | 528

(2) INFORMATION FOR SEQ ID NO:3:

(i) SEQUENCE CHARACTERISTICS:
        (A) LENGTH: 528 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:3:

| | | | | | |
|---|---|---|---|---|---|
| TCCCGTGCTC | ACCAGCACTC | CATGGAAACC | CGTACCCCGG | ACATCAACCC | GGCTTGGTAC | 60
| ACCGGTCGTG | GTATCCGTCC | GGTTGGTCGT | TTCTGCCCCG | AGGATGGCGG | CAGCGGCGCC | 120
| TTCCCGCCCG | GCCACTTCAA | GGACCCCAAG | CGGCTGTACT | GCAAAAACGG | GGGCTTCTTC | 180
| CTGCGCATCC | ACCCCGACGG | CCGAGTTGAC | GGGGTCCGGG | AGAAGAGCGA | CCCTCACATC | 240
| AAGCTACAAC | TTCAAGCAGA | AGAGAGAGGA | GTTGTGTCTA | TCAAAGGAGT | GAGCGCTAAT | 300
| CGTTACCTGG | CTATGAAGGA | AGATGGAAGA | TTACTAGCTT | CTAAGTCTGT | TACGGATGAG | 360

```
TGTTTCTTTT TTGAACGATT GGAATCTAAT AACTACAATA CTTACCGGTC AAGGAAATAC      420

ACCAGTTGGT ATGTGGCACT GAAACGAACT GGGCAGTATA AACTTGGATC CAAAACAGGA      480

CCTGGGCAGA AAGCTATACT TTTTCTTCCA ATGTCTGCTA AGAGCTGC                   528

(2) INFORMATION FOR SEQ ID NO:4:

(i) SEQUENCE CHARACTERISTICS:
        (A) LENGTH: 528 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:4:

TCCCGTGCTC ACCAGCACTC CATGGAAACC CGTACCCCGG ACATCAACCC GGCTTGGTAC      60

ACCGGTCGTG GTATCCGTCC GGTTGGTCGT TTCTGTCCCG AGGATGGCGG CAGCGGCGCC     120

TTCCCGCCCG GCCACTTCAA GGACCCCAAG CGGCTGTACT GCAAAAACGG GGGCTTCTTC     180

CTGCGCATCC ACCCCGACGG CCGAGTTGAC GGGGTCCGGG AGAAGAGCGA CCCTCACATC     240

AAGCTACAAC TTCAAGCAGA AGAGAGAGGA GTTGTGTCTA TCAAAGGAGT GAGCGCTAAT     300

CGTTACCTGG CTATGAAGGA AGATGGAAGA TTACTAGCTT CTAAGTCTGT TACGGATGAG     360

TGTTTCTTTT TTGAACGATT GGAATCTAAT AACTACAATA CTTACCGGTC AAGGAAATAC     420

ACCAGTTGGT ATGTGGCACT GAAACGAACT GGGCAGTATA AACTTGGATC CAAAACAGGA     480

CCTGGGCAGA AAGCTATACT TTTTCTTCCA ATGTCTGCTA AGAGCTGC                  528

(2) INFORMATION FOR SEQ ID NO:5:

(i) SEQUENCE CHARACTERISTICS:
        (A) LENGTH: 528 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:5:

TCCCGTACCC ACCGTCACTC CATGGAAATC CGTACCCCGG ACATCAACCC GGCTTGGTAC      60

GCTTCCCGTG GTATCCGTCC GGTTGGTCGT TTCTGCCCCG AGGATGGCGG CAGCGGCGCC     120

TTCCCGCCCG GCCACTTCAA GGACCCCAAG CGGCTGTACT GCAAAAACGG GGGCTTCTTC     180

CTGCGCATCC ACCCCGACGG CCGAGTTGAC GGGGTCCGGG AGAAGAGCGA CCCTCACATC     240

AAGCTACAAC TTCAAGCAGA AGAGAGAGGA GTTGTGTCTA TCAAAGGAGT GAGCGCTAAT     300

CGTTACCTGG CTATGAAGGA AGATGGAAGA TTACTAGCTT CTAAGTCTGT TACGGATGAG     360

TGTTTCTTTT TTGAACGATT GGAATCTAAT AACTACAATA CTTACCGGTC AAGGAAATAC     420

ACCAGTTGGT ATGTGGCACT GAAACGAACT GGGCAGTATA AACTTGGATC CAAAACAGGA     480

CCTGGGCAGA AAGCTATACT TTTTCTTCCA ATGTCTGCTA AGAGCTGC                  528

(2) INFORMATION FOR SEQ ID NO:6:

(i) SEQUENCE CHARACTERISTICS:
        (A) LENGTH: 528 base pairs
        (B) TYPE: nucleic acid
        (C) STRANDEDNESS: double
        (D) TOPOLOGY: linear (ii) MOLECULE TYPE: synthetic DNA
```

(xi) SEQUENCE DESCRIPTION: SEQ ID NO:6:

```
TCCCGTACCC ACCGTCACTC CATGGAAATC CGTACCCCGG ACATCAACCC GGCTTGGTAC      60

GCTTCCCGTG GTATCCGTCC GGTTGGTCGT TTCTGTCCCG AGGATGGCGG CAGCGGCGCC     120

TTCCCGCCCG GCCACTTCAA GGACCCCAAG CGGCTGTACT GCAAAAACGG GGGCTTCTTC     180

CTGCGCATCC ACCCCGACGG CCGAGTTGAC GGGGTCCGGG AGAAGAGCGA CCCTCACATC     240

AAGCTACAAC TTCAAGCAGA AGAGAGAGGA GTTGTGTCTA TCAAAGGAGT GAGCGCTAAT     300

CGTTACCTGG CTATGAAGGA AGATGGAAGA TTACTAGCTT CTAAGTCTGT TACGGATGAG     360

TGTTTCTTTT TTGAACGATT GGAATCTAAT AACTACAATA CTTACCGGTC AAGGAAATAC     420

ACCAGTTGGT ATGTGGCACT GAAACGAACT GGGCAGTATA AACTTGGATC CAAAACAGGA     480

CCTGGGCAGA AAGCTATACT TTTTCTTCCA ATGTCTGCTA AGAGCTGC                  528
```

(2) INFORMATION FOR SEQ ID NO:7:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Ser Arg Ala His Gln His Ser Met Glu Ile Arg Thr Pro Asp Ile Asn
1               5                   10                  15

Pro Ala Trp Tyr Ala Gly Arg Gly Ile Arg Pro Val Gly Arg Phe
            20                  25                  30
```

(2) INFORMATION FOR SEQ ID NO:8:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30
```

(2) INFORMATION FOR SEQ ID NO:9:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30
```

(2) INFORMATION FOR SEQ ID NO:10:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (ii) MOLECULE TYPE: synthetic DNA (xi) SEQUENCE DESCRIPTION: SEQ ID NO:10:

CTAGAAAGGA GATATACACT ATGTCCCGTG CTCACCAGC          39

(2) INFORMATION FOR SEQ ID NO:11:

(i) SEQUENCE CHARACTERISTICS:
           (A) LENGTH: 42 base pairs
           (B) TYPE: nucleic acid
           (C) STRANDEDNESS: single
           (D) TOPOLOGY: linear (ii) MOLECULE TYPE: synthetic DNA (xi) SEQUENCE DESCRIPTION: SEQ ID NO:11:

ACTCCATGGA AATCCGTACC CCGGACATCA ACCCGGCTTG GT      42

(2) INFORMATION FOR SEQ ID NO:12:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (ii) MOLECULE TYPE: synthetic DNA (xi) SEQUENCE DESCRIPTION: SEQ ID NO:12:

ACGCTGGTCG TGGTATCCGT CCGGTTGGTC GTTTCTGCC          39

(2) INFORMATION FOR SEQ ID NO:13:

(i) SEQUENCE CHARACTERISTICS:
           (A) LENGTH: 45 base pairs
           (B) TYPE: nucleic acid
           (C) STRANDEDNESS: single
           (D) TOPOLOGY: linear (ii) MOLECULE TYPE: synthetic DNA (xi) SEQUENCE DESCRIPTION: SEQ ID NO:13:

TCCATGGAGT GCTGGTGAGC ACGGGACATA GTGTATATCT CCTTT   45

(2) INFORMATION FOR SEQ ID NO:14:

(i) SEQUENCE CHARACTERISTICS:
           (A) LENGTH: 42 base pairs
           (B) TYPE: nucleic acid
           (C) STRANDEDNESS: single
           (D) TOPOLOGY: linear (ii) MOLECULE TYPE: synthetic DNA (xi) SEQUENCE DESCRIPTION: SEQ ID NO:14:

CGACCAGCGT ACCAAGCCGG GTTGATGTCC GGGGTACGGA TT      42

(2) INFORMATION FOR SEQ ID NO:15:

(i) SEQUENCE CHARACTERISTICS:
           (A) LENGTH: 33 base pairs
           (B) TYPE: nucleic acid (C) STRANDEDNESS: single
        (D) TOPOLOGY: linear (ii) MOLECULE TYPE: synthetic DNA (xi) SEQUENCE DESCRIPTION: SEQ ID NO:15:

TCGGGGCAGA AACGACCAAC CGGACGGATA CCA                           33

(2) INFORMATION FOR SEQ ID NO:16:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:16:

CTAGAAAGGA GATATACACT ATGTCCCGTG CTCACCAGC                     39

(2) INFORMATION FOR SEQ ID NO:17:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:17:

ACTCCATGGA AACCCGTACC CCGGACATCA ACCCGGCTTG GT                 42

(2) INFORMATION FOR SEQ ID NO:18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:18:

ACACCGGTCG TGGTATCCGT CCGGTTGGTC GTTTCTGCC                     39

(2) INFORMATION FOR SEQ ID NO:19:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:19:

TCCATGGAGT GCTGGTGAGC ACGGGACATA GTGTATATCT CCTTT              45

(2) INFORMATION FOR SEQ ID NO:20:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:20:

CGACCGGTGT ACCAAGCCGG GTTGATGTCC GGGGTACGGG TT                     42

(2) INFORMATION FOR SEQ ID NO:21:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:21:

TCGGGGCAGA AACGACCAAC CGGACGGATA CCA                              33

(2) INFORMATION FOR SEQ ID NO:22:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:22:

CTAGAAAGGA GATATACACT ATGTCCCGTA CCCACCGTC                         39

(2) INFORMATION FOR SEQ ID NO:23:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:23:

ACTCCATGGA AATCCGTACC CCGGACATCA ACCCGGCTTG GT                     42

(2) INFORMATION FOR SEQ ID NO:24:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:24:

ACGCTTCCCG TGGTATCCGT CCGGTTGGTC GTTTCTGCC                         39

(2) INFORMATION FOR SEQ ID NO:25:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:25:

TCCATGGAGT GACGGTGGGT ACGGGACATA GTGTATATCT CCTTT                  45

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:26:

CGGGAAGCGT ACCAAGCCGG GTTGATGTCC GGGGTACGGA TT                   42

(2) INFORMATION FOR SEQ ID NO:27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:27:

TCGGGGCAGA AACGACCAAC CGGACGGATA CCA                            33

(2) INFORMATION FOR SEQ ID NO:28:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 10
        (D) OTHER INFORMATION: /product= "Ala or Thr"

(ix) FEATURE:
        (A) NAME/KEY: Modified-site
        (B) LOCATION: 11
        (D) OTHER INFORMATION: /product= "Gly or Ser"

(ix) FEATURE:
        (A) NAME/KEY: Modified-site
        (B) LOCATION: 21
        (D) OTHER INFORMATION: /product= "Gly-OH or Gly-Arg"

(xi) SEQUENCE DESCRIPTION: SEQ ID NO:28:

Thr Pro Asp Ile Asn Pro Ala Trp Tyr Xaa Xaa Arg Gly Ile Arg Pro
1             5                   10               15

Val Gly Arg Phe Xaa
        20

(2) INFORMATION FOR SEQ ID NO:29:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Ser Arg Ala His Gln His Ser Met Glu Ile Arg Thr Pro Asp Ile Asn

```
1               5                   10                  15
Pro Ala Trp Tyr Ala Gly Arg Gly Ile Arg Pro Val Gly
            20                  25
```

(2) INFORMATION FOR SEQ ID NO:30:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Thr Pro Asp Ile Asn Pro Ala Trp Tyr Ala Gly Arg Gly Ile Arg Pro
1               5                   10                  15
Val Gly Arg
```

(2) INFORMATION FOR SEQ ID NO:31:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
Ser Arg Ala His Gln His Ser Met Glu Ile Arg Thr Pro Asp Ile Asn
1               5                   10                  15
Pro Ala Trp Tyr Ala Gly Arg Gly Ile Arg Pro Val Gly Arg Phe
            20                  25                  30
```

(2) INFORMATION FOR SEQ ID NO:32:

(i) SEQUENCE CHARACTERISTICS:
        (A) LENGTH: 32 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Ser Arg Ala His Gln His Ser Met Glu Ile Arg Thr Pro Asp Ile Asn
1               5                   10                  15
Pro Ala Trp Tyr Ala Gly Arg Gly Ile Arg Pro Val Gly Arg Phe Gly
            20                  25                  30
```

(2) INFORMATION FOR SEQ ID NO:33:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
Ser Arg Ala His Gln His Ser Met Glu Ile Arg Thr Pro Asp Ile Asn
1               5                   10                  15
Pro Ala Trp Tyr Ala Gly Arg Gly Ile Arg Pro Val Gly Arg Phe Gly
            20                  25                  30
```

Arg (2) INFORMATION FOR SEQ ID NO:34:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

Thr Pro Asp Ile Asn Pro Ala Trp Tyr Ala Gly Arg Gly Ile Arg Pro
1               5                   10                  15

Val Gly Arg Phe
            20

(2) INFORMATION FOR SEQ ID NO:35:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

Thr Pro Asp Ile Asn Pro Ala Trp Tyr Ala Gly Arg Gly Ile Arg Pro
1               5                   10                  15

Val Gly Arg Phe Gly
            20

(2) INFORMATION FOR SEQ ID NO:36:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

Thr Pro Asp Ile Asn Pro Ala Trp Tyr Ala Gly Arg Gly Ile Arg Pro
1               5                   10                  15

Val Gly Arg Phe Gly Arg
            20

(2) INFORMATION FOR SEQ ID NO:37:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
                20                  25                  30

(2) INFORMATION FOR SEQ ID NO:38:

(i) SEQUENCE CHARACTERISTICS:
        (A) LENGTH: 32 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

```
Ser Arg Ala His Gln His Ser Met Glu Thr Arg Thr Pro Asp Ile Asn
1               5                   10                  15
Pro Ala Trp Tyr Thr Gly Arg Gly Ile Arg Pro Val Gly Arg Phe Gly
            20                  25                  30
```

(2) INFORMATION FOR SEQ ID NO:39:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

```
Ser Arg Ala His Gln His Ser Met Glu Thr Arg Thr Pro Asp Ile Asn
1               5                   10                  15
Pro Ala Trp Tyr Thr Gly Arg Gly Ile Arg Pro Val Gly Arg Phe Gly
            20                  25                  30
Arg
```

(2) INFORMATION FOR SEQ ID NO:40:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

```
Thr Pro Asp Ile Asn Pro Ala Trp Tyr Thr Gly Arg Gly Ile Arg Pro
1               5                   10                  15
Val Gly Arg Phe
            20
```

(2) INFORMATION FOR SEQ ID NO:41:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

```
Thr Pro Asp Ile Asn Pro Ala Trp Tyr Thr Gly Arg Gly Ile Arg Pro
1               5                   10                  15
Val Gly Arg Phe Gly
            20
```

(2) INFORMATION FOR SEQ ID NO:42:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

Thr Pro Asp Ile Asn Pro Ala Trp Tyr Thr Gly Arg Gly Ile Arg Pro
1               5                   10                  15

Val Gly Arg Phe Gly Arg
            20

(2) INFORMATION FOR SEQ ID NO:43:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

(2) INFORMATION FOR SEQ ID NO:44:

(i) SEQUENCE CHARACTERISTICS:
        (A) LENGTH: 32 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe Gly
            20                  25                  30

(2) INFORMATION FOR SEQ ID NO:45:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:45:

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe Gly
            20                  25                  30

Arg (2) INFORMATION FOR SEQ ID NO:46:

```
       (i) SEQUENCE CHARACTERISTICS:
           (A) LENGTH: 20 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:46:

Thr Pro Asp Ile Asn Pro Ala Trp Tyr Ala Ser Arg Gly Ile Arg Pro
1               5                  10                  15

Val Gly Arg Phe
           20

(2) INFORMATION FOR SEQ ID NO:47:

(i) SEQUENCE CHARACTERISTICS:
           (A) LENGTH: 21 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:47:

Thr Pro Asp Ile Asn Pro Ala Trp Tyr Ala Ser Arg Gly Ile Arg Pro
1               5                  10                  15

Val Gly Arg Phe Gly
           20

(2) INFORMATION FOR SEQ ID NO:48:

(i) SEQUENCE CHARACTERISTICS:
           (A) LENGTH: 22 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:48:

Thr Pro Asp Ile Asn Pro Ala Trp Tyr Ala Ser Arg Gly Ile Arg Pro
1               5                  10                  15

Val Gly Arg Phe Gly Arg
           20

(2) INFORMATION FOR SEQ ID NO:49:

(i) SEQUENCE CHARACTERISTICS:
           (A) LENGTH: 146 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:49:

Pro Ala Leu Pro Glu Asp Gly Gly Ser Gly Ala Phe Pro Pro Gly His
1               5                  10                  15

Phe Lys Asp Pro Lys Arg Leu Tyr Cys Lys Asn Gly Gly Phe Phe Leu
                20                  25                  30

Arg Ile His Pro Asp Gly Arg Val Asp Gly Val Arg Glu Lys Ser Asp
            35                  40                  45

Pro His Ile Lys Leu Gln Leu Gln Ala Glu Glu Arg Gly Val Val Ser
    50                  55                  60
```

```
Ile Lys Gly Val Ser Ala Asn Arg Tyr Leu Ala Met Lys Glu Asp Gly
 65                  70                  75                  80

Arg Leu Leu Ala Ser Lys Ser Val Thr Asp Glu Cys Phe Phe Phe Glu
                 85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
            115                 120                 125

Lys Thr Gly Pro Gly Gln Lys Ala Ile Leu Phe Leu Pro Met Ser Ala
130                 135                 140

Lys Ser
145
```

(2) INFORMATION FOR SEQ ID NO:50:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:50:

```
Leu Leu Arg Pro
 1
```

(2) INFORMATION FOR SEQ ID NO:51:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:51:

```
Val Ala Leu Ala Ala Pro Leu Ala Pro Arg
 1               5                  10
```

(2) INFORMATION FOR SEQ ID NO:52:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:52:

```
TCTAGAAAGG AGATATACAC TATGTCCCGT GCTCACCAGC ACTCCATGGA AATCCGTACC        60
CCGGACATCA ACCCGGCTTG GTACGCTGGT CGTGGTATCC GTCCGGTTGG TCGTTTCTGC       120
CCCGAG                                                                  126
```